United States Patent
Balbierz et al.

(10) Patent No.: US 6,869,430 B2
(45) Date of Patent: Mar. 22, 2005

(54) TISSUE BIOPSY AND TREATMENT APPARATUS AND METHOD

(75) Inventors: Daniel J. Balbierz, Redwood City, CA (US); Theodore Johnson, San Francisco, CA (US)

(73) Assignee: Rita Medical Systems, Inc., Mountain View, CA (US)

( * ) Notice: Subject to any disclaimer, the term of this patent is extended or adjusted under 35 U.S.C. 154(b) by 88 days.

(21) Appl. No.: 09/823,903

(22) Filed: Mar. 30, 2001

(65) Prior Publication Data

US 2002/0026127 A1 Feb. 28, 2002

Related U.S. Application Data

(60) Provisional application No. 60/193,544, filed on Mar. 31, 2000.

(30) Foreign Application Priority Data

Mar. 23, 2000 (JP) .......................... 2000-087109

(51) Int. Cl.[7] .............................................. A61B 18/18
(52) U.S. Cl. ...................................................... 606/41
(58) Field of Search .............................. 606/33–52, 41, 606/12; 600/567

(56) References Cited

U.S. PATENT DOCUMENTS

| | | | |
|---|---|---|---|
| 4,281,645 A | 8/1981 | Jobsis | |
| 4,416,285 A | 11/1983 | Shaw et al. | |
| 4,515,165 A | 5/1985 | Carroll | |
| 5,088,493 A | 2/1992 | Giannini et al. | |
| 5,090,415 A | 2/1992 | Yamashita et al. | |
| 5,131,398 A | 7/1992 | Alfano et al. | |
| 5,218,962 A | 6/1993 | Mannheimer et al. | |
| 5,219,345 A | 6/1993 | Potter | |
| 5,280,788 A | 1/1994 | Janes et al. | |
| 5,321,501 A | 6/1994 | Swanson et al. | |
| 5,413,108 A | 5/1995 | Alfano | |
| 5,421,337 A | 6/1995 | Richards-Kortum et al. | |
| 5,697,373 A | 12/1997 | Richards-Kortum et al. | |
| 5,735,847 A | * 4/1998 | Gough et al. | 606/41 |
| 5,762,609 A | * 6/1998 | Benaron et al. | 600/473 |
| 5,769,791 A | * 6/1998 | Benaron et al. | 600/473 |
| 5,772,407 A | 6/1998 | Kato et al. | |
| 5,782,770 A | 7/1998 | Mooradian et al. | |
| 5,785,658 A | 7/1998 | Benaron et al. | |
| 5,853,370 A | 12/1998 | Chance et al. | |
| 6,167,297 A | 12/2000 | Benaron | |
| 6,200,310 B1 | * 3/2001 | Ben-Haim et al. | 606/10 |
| 6,409,722 B1 | * 6/2002 | Hoey et al. | 606/34 |

FOREIGN PATENT DOCUMENTS

| | | |
|---|---|---|
| WO | WO 92/17108 | 10/1992 |
| WO | WO 93/03672 | 3/1993 |
| WO | WO 97/37723 | 10/1997 |
| WO | WO 98/01074 | 1/1998 |
| WO | WO 00/00098 | 1/2000 |
| WO | WO 00/13603 | 3/2000 |

* cited by examiner

*Primary Examiner*—Michael Peffley
*Assistant Examiner*—Pete Vrettakos
(74) *Attorney, Agent, or Firm*—Jacqueline F. Mahoney; Peter J. Dehlinger; Perkins Coie LLP

(57) ABSTRACT

An embodiment of the invention provides a tissue biopsy and treatment apparatus that comprises an elongated delivery device that is positionable in tissue and includes a lumen. A sensor array having a plurality of resilient members is deployable from the elongated delivery device. At least one of the plurality of resilient members is positionable in the elongated delivery device in a compacted state and deployable with curvature into tissue from the elongated delivery device in a deployed state. At least one of the plurality of resilient members includes at least one of a sensor, a tissue piercing distal end or a lumen. The sensor array has a geometric configuration adapted to volumetrically sample tissue at a tissue site to differentiate or identify tissue at the target tissue site. At least one energy delivery device is coupled to one of the sensor array, at least one of the plurality of resilient members or the elongated delivery device.

52 Claims, 23 Drawing Sheets

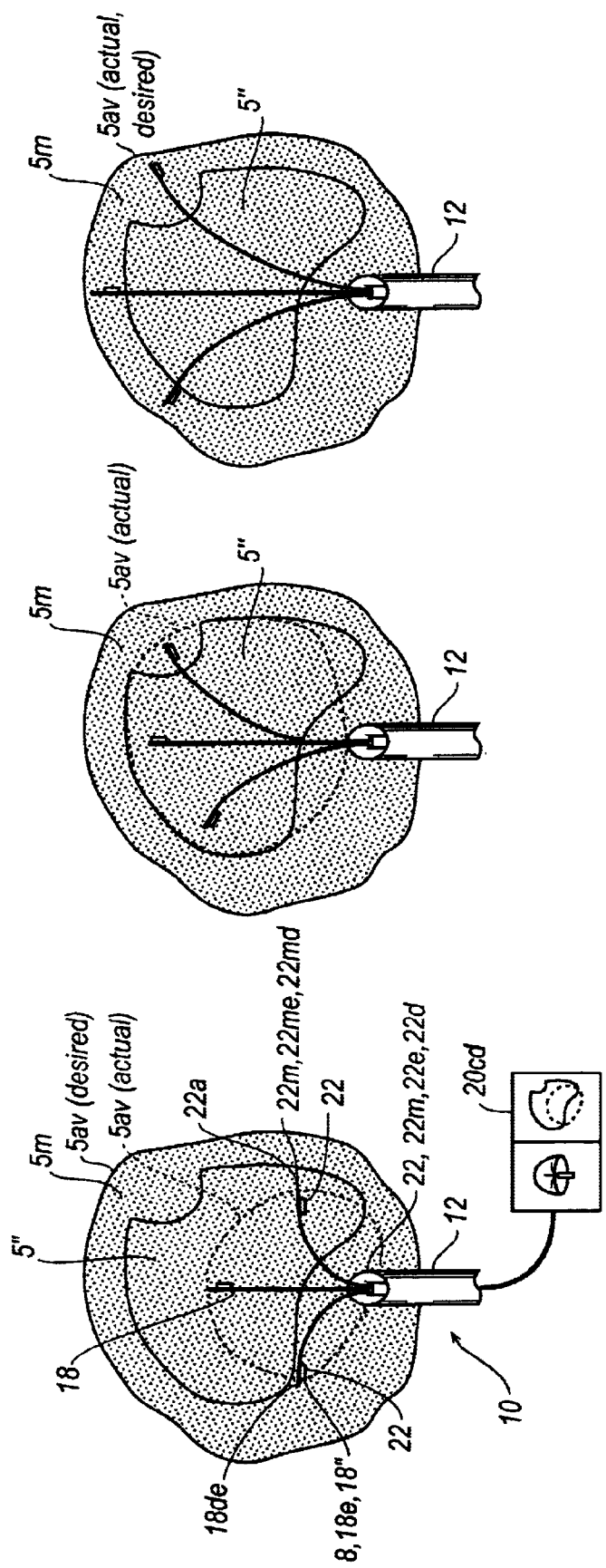

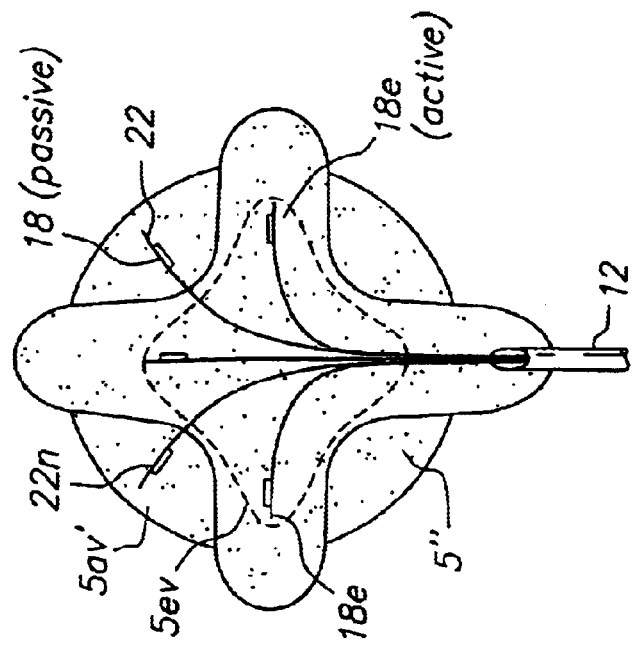
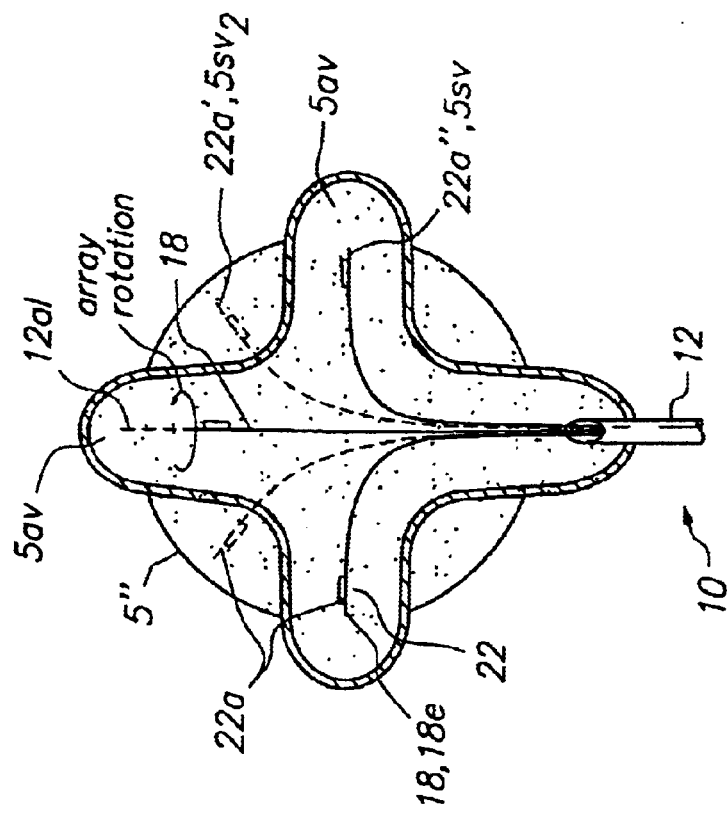

TISSUE BIOPSY AND TREATMENT APPARATUS AND METHOD

CROSS-RELATED APPLICATIONS

This application claims the benefit of priority to U.S. Provisional Application Ser. No. 60/193,544 filed Mar. 31, 2000, entitled "Tissue Biopsy, Monitoring and Treatment Apparatus and Method", which is fully incorporated by reference herein.

FIELD OF THE INVENTION

This invention relates generally to a method for performing an in vivo tissue biopsy sample using minimally invasive methods. More particularly, the invention to relates to method and apparatus for performing in vivo tissue biopsy using optical methods. Still more particularly, the invention relates to a method and apparatus for performing an in vivo tissue biopsy to discriminate between diseased and healthy tissue and facilitate tissue treatment.

BACKGROUND OF THE INVENTION

Various ablative procedures can be used to treat diseased and/or abnormal tissue. These methods cause physiological and structural changes intended to cause necrosis of the selected target tissue. During ablative procedures of diseased and other abnormal tissue, clinicians encounter numerous difficulties and challenges, these include (i) locating the target tissue, (ii) the need to perform a biopsy and diagnose diseased tissue versus healthy tissue, (iii) correct device placement, (iv) monitoring ablation progress, (v) assuring a (healthy tissue) margin, and (vi) assessing the completed ablation. Current ablative technologies have failed to recognize and therefore, properly address these requirements.

SUMMARY OF THE INVENTION

An embodiment of the invention provides a tissue biopsy and treatment apparatus that comprises an elongated delivery device that is positionable in tissue and includes a lumen. A sensor array having a plurality of resilient members is deployable from the elongated delivery device. At least one of the plurality of resilient members is positionable in the elongated delivery device in a compacted state and deployable with curvature into tissue from the elongated delivery device in a deployed state. At least one of the plurality of resilient members includes at least one of a sensor, a tissue piercing distal end or a lumen. The sensor array has a geometric configuration adapted to volumetrically sample tissue at a tissue site to differentiate or identify tissue at the target tissue site. At least one energy delivery device is coupled to one of the sensor array, at least one of the plurality of resilient members or the elongated delivery device.

Another embodiment provides a tissue biopsy and treatment apparatus that comprises an elongated delivery device that is positionable in tissue and includes a lumen. A sensor array having a plurality of resilient members is deployable from the elongated delivery device. At least one of the plurality of resilient members is positionable in the elongated delivery device in a compacted state and deployable with curvature into tissue from the elongated delivery device in a deployed state. At least one of the plurality of resilient members includes at least one of a sensor, a tissue piercing distal end or a lumen. The sensor array has a geometric configuration adapted to volumetrically sample and measure a spectral profile of at least one portion of a tissue site to differentiate or identify tissue at the tissue site. At least one energy delivery device is coupled to one of the sensor array, at least one of the plurality of resilient members or the elongated delivery device.

Yet another embodiment of the invention provides a tissue biopsy and treatment apparatus that comprises an elongated delivery device that is positionable in tissue and includes a lumen. A sensor array having a plurality of resilient members is deployable from the elongated delivery device. At least one of the plurality of resilient members is positionable in the elongated delivery device in a compacted state and deployable with curvature into tissue from the elongated delivery device in a deployed state. At least one of the plurality of resilient members is maneuverable in tissue and includes a lumen and an optical sensor member positionable within the lumen. At least one of the plurality of resilient members includes at least one of a sensor, a tissue piercing distal end or a lumen. The sensor array has a geometric configuration adapted to volumetrically sample tissue at a tissue site to differentiate or identify tissue at the target tissue site. At least one energy delivery device is coupled to one of the sensor array, at least one of the plurality of resilient members or the elongated delivery device.

Still yet another embodiment of the invention includes a tissue biopsy and treatment apparatus that comprises an elongated delivery device that is positionable in tissue and includes a lumen. A sensor array having a plurality of resilient members is deployable from the elongated delivery device. At least one of the plurality of resilient members is positionable in the elongated delivery device in a compacted state and deployable with curvature into tissue from the elongated delivery device in a deployed state. At least one of the plurality of resilient members includes at least one of a sensor, a tissue piercing distal end or a lumen. The sensor array is configured to detect a marling agent and has a geometric configuration adapted to volumetrically sample tissue at a tissue site to differentiate or identify tissue at the target tissue site. At least one energy delivery device is coupled to one of the sensor array, at least one of the plurality of resilient members or the elongated delivery device. Also a source of marking agent is fluidically coupled to at least one of the elongated member or at least one member of the plurality of resilient members.

Yet another embodiment of the invention includes a method for tumor detection, wherein a primary optically labeled marker or antibody is infused into a patient or injected into a target tissue or organ site containing a tumor and specifically binds to a marker produced by or associated with a tumor. The target tissue or organ site is scanned with a biopsy ablation apparatus including a sensor array and the binding sites of the labeled marker antibody are located by detecting elevated levels of optical label signal intensity at such sites with the sensor array. This information can be digitally stored and displayed on a monitor device to accurately position the biopsy ablation apparatus within the tumors to deliver energy to necrose or ablate the tumor resulting in an ablation volume. A second marker which binds or reacts with necrosed tumor tissue can infused or injected into the tumor site before, during or after the delivery of ablating energy. The sensor array is utilized to detect the signal from the second marker ablation volume and this signal digitally stored and superimpose the display over tumor volume image so as to determine the size of the ablation volume relative to the tumor volume. This embodiment provides two key benefit to the physician: (i) visual confirmation that the tumor has been completely ablated/ necrosed, (ii) selective control over the amount of healthy tissue margin that is ablated beyond the tumor volume to improve clinical outcomes of the procedure.

BRIEF DESCRIPTION OF THE FIGURES

FIG. 8a illustrates an embodiment having a centrally positioned emitter member surrounded by detector members; FIG. 8b illustrates an embodiment having centrally a positioned detector member surrounded by emitter members; FIG. 8c illustrates an embodiment having emitters 22me and detectors 22md located in linear arrangements that are substantially perpendicular or have a selectable angle; FIG. 8d illustrates an embodiment having multiple and independently positionable and rotatable sensor arrays.

FIGS. 16a–16c are perspective views illustrating use of the sensor array to assure proper placement of the energy delivery members in the tumor mass in an embodiment of a method of the invention.

FIGS. 17a and 17b are perspective views illustrating use of the sensor array to detect an incomplete ablation in embodiments of a method of the invention.

FIGS. 21a–21f are lateral views illustrating various configurations of the electrode including ring-like, ball, hemispherical, cylindrical, conical and needle-like.

DETAILED DESCRIPTION

Embodiments of the present invention provide a method and apparatus to optically biopsy a tissue and use the information to diagnose a tumor, accurately position an energy delivery device, visually monitor and confirm complete ablation of the tumor. Further embodiments of the invention include one or more sensing members or sensing arrays that can be deployed independently or simultaneously to enable probing of target tissue by optical or other means.

Deployment of each array is controlled such that telemetry can be used with optical, temperature and impedance feedback to both identify tissue and map the topography of tissue types and structures to facilitate proper placement of an energy delivery device to ablate the tumor. These and other embodiments of the invention allow for the control and determination of a clinical endpoint while significantly reducing the risk of incomplete ablation or unwanted damage to critical anatomical structures due to improper device placement.

Specific embodiments are configured to utilize inputs from the sensor to distinguish and identify the distinct spectral profiles that are generated by different tissues. The apparatus is further configured to employ analytical methods to compare these profiles and utilize them to accurately identify and distinguish between tissue types. Such tissue comparison and identification is particularly applicable to the detection of metastases and other types of tumors. This is due to the fact that metastases are growths of tissue from cells originating in a different part of the body from the subsequent tumor site that they cause. As such these different body tissues have different pathological features, the spectral profile comparison can be used to discern a metastatic or other non-native tumor within the target tissue sample.

Figure 1:
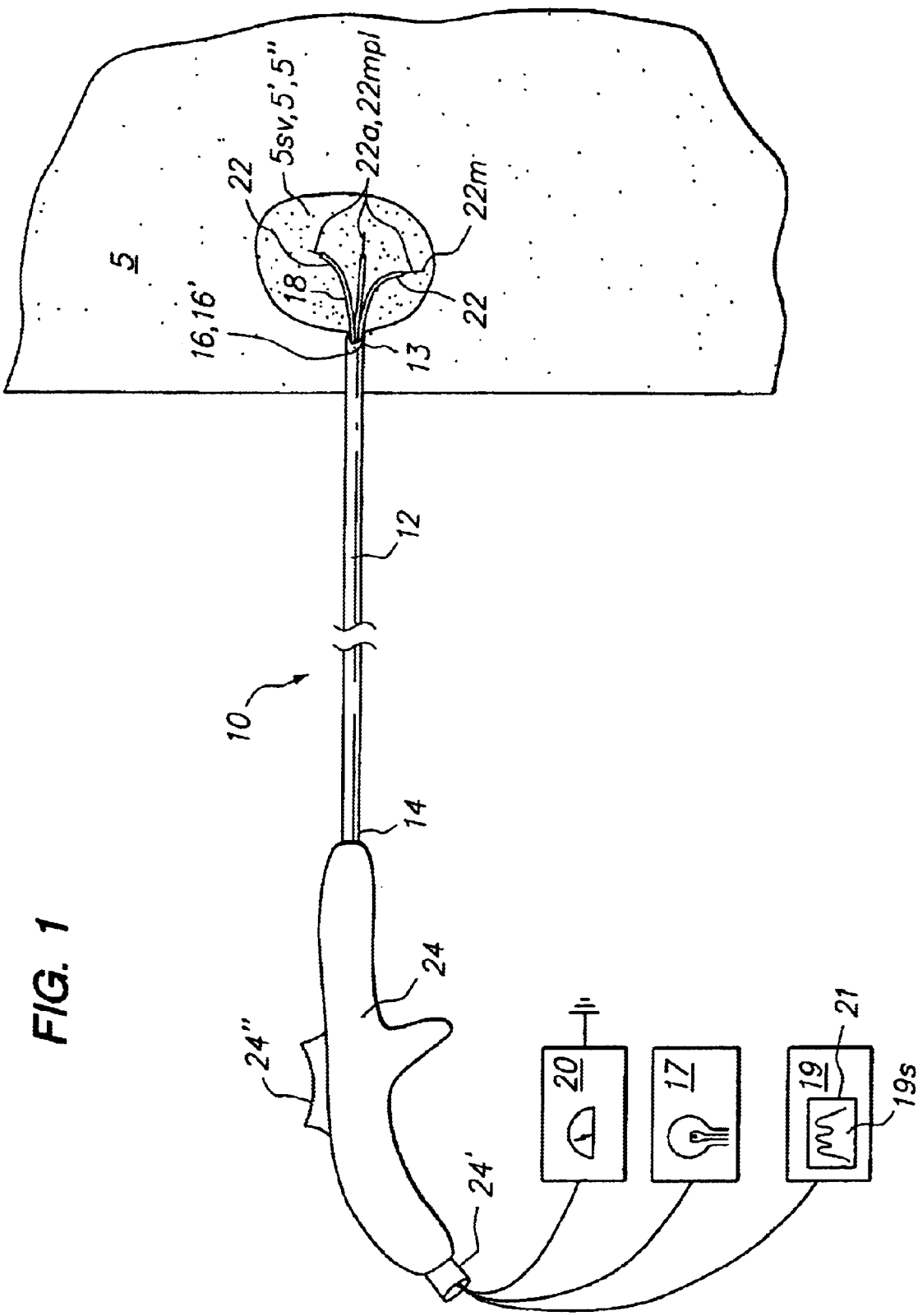
FIG. 1 is a lateral view illustrating the placement of an embodiment of a tissue biopsy and treatment apparatus at a tissue site.
Figure 2:
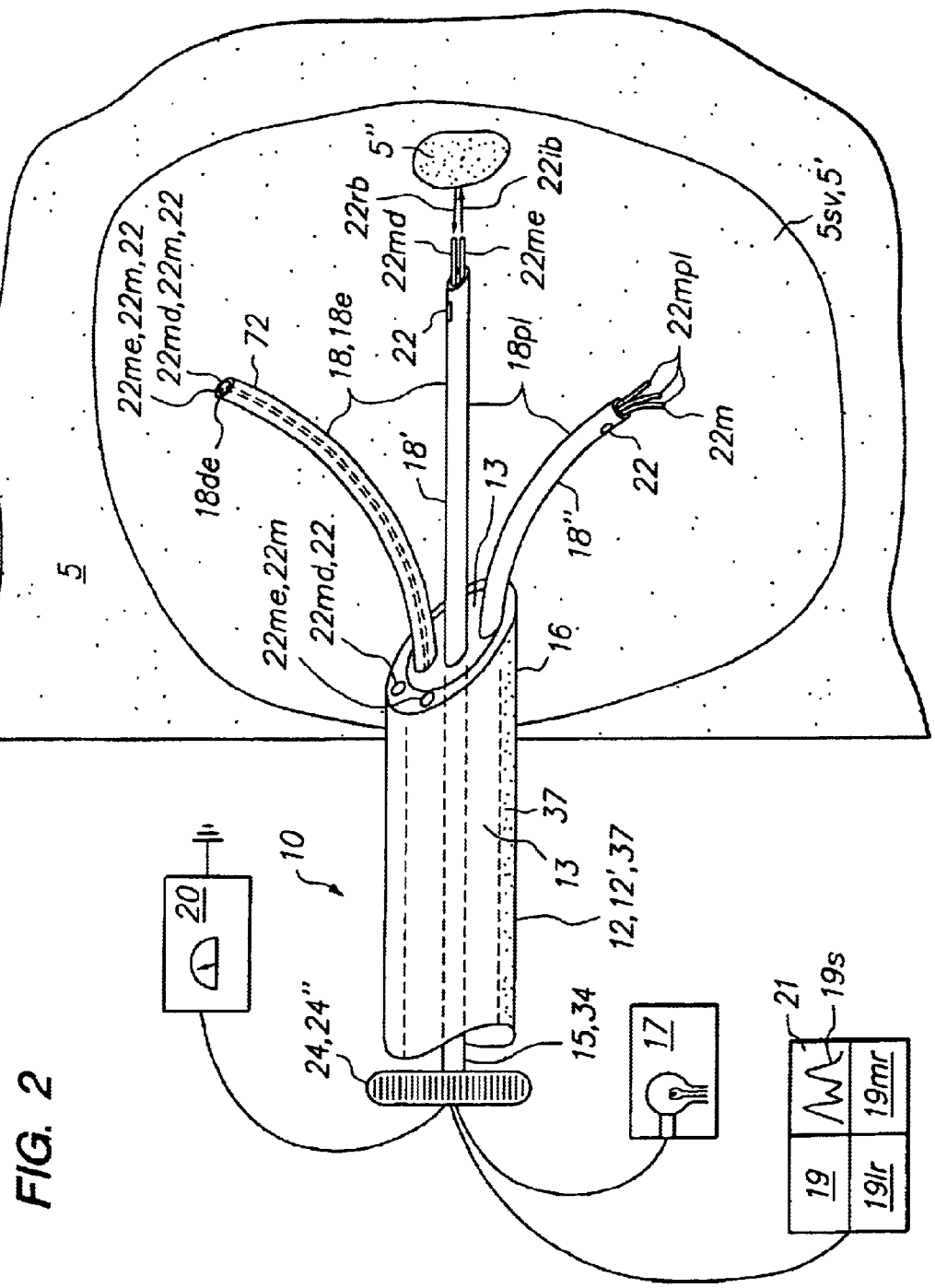
FIG. 2 is a lateral view illustrating the components of an embodiment of a biopsy and treatment apparatus including the elongated member, sensor array, resilient members and energy delivery device and advancement member.

FIG. 1 shows an embodiment of a tissue biopsy and treatment apparatus 10 configured to optically biopsy and treat a tumor mass 5" in a target tissue site 5' by volumetrically sampling the tissue mass and delivering energy or other treatment to produce an ablation volume 5av. Referring now to FIGS. 1 and 2, an embodiment of biopsy treatment apparatus 10 comprises an elongated member or introducer 12 having a lumen 13, a proximal portion 14, a distal end 16, one or more resilient members 18 positionable in lumens 13 and one or more sensing members 22m positionable in lumens 72 disposed within members 18. Distal end 16 may be sufficiently sharp to penetrate tissue including fibrous and/or encapsulated tumor masses, bone, cartilage and muscle. Lumens 13 may extend over all or a portion of the length of introducer 12. Members 18 can comprise a plurality 18pl of resilient members 18 configured to be positionable in lumen 13 and advanceable in and out of distal end 16 by an advancement device 15 or advancement member 34 or other means described herein. Resilient members 18 can be deployed with curvature from introducer 12 to collectively define a volume 5av in target tissue site 5'. In an embodiment all, or a portion, of one or more members 18 can be an energy delivery device or energy delivery member 18e described herein. Energy delivery device 18e can be coupled to an energy source or power supply 20 and can also include one or more lumens 72.

In various embodiments, introducer 12 can be flexible, articulated and steerable and can contain fiber optics (both illumination and imaging fibers), fluid and gas paths, and sensor and electronic cabling. In an embodiment introducer 12 can be configured to both pierce tissue and also be maneuverable within tissue. This can be achieved through the use of flexible portions coupled to a tissue piercing distal end 16 that can be a needle or trocar tip integral or joined to introducer 12. Introducer 12 can be sufficiently flexible to move in any desired direction through tissue to a desired tissue site 5'. In related embodiments, introducer 12 is sufficiently flexible to reverse its direction of travel and move in direction back upon itself. This can be achieved through the use of flexible materials and/or deflecting mechanisms described herein. Also, introducer 12 can be coupled at its proximal end 14 to a handle 24 or handpiece 24. Handpiece 24 can be detachable and can include ports 24' and actuators 24".

One or more sensors 22 can be coupled to introducer 12, resilient members 18 or energy delivery device 18e. In an embodiment, sensors 22 can comprise one or more sensing members 22m that can be positionable within lumens 72 of members 18 and configured to be advanceable in and out of individual members 18 or can be coupled to an exterior of resilient member 18. Sensing members 22m can comprise a plurality of members 22mpl positioned in multiple resilient members 18. Sensing members 22m, or sensors 22 coupled to resilient members 18 can be deployed independently or simultaneously to enable probing of target tissue 5' in multiple locations. Deployment of sensing member 22m or sensors 22 can be controlled such that telemetry can be used with optical, temperature and impedance feedback to identify tissue types and map the topography of tissue masses, tumors or tissue structures.

33. Sensing members 22m can also be deployed with curvature from members 18 to collectively define a volume 5sv (also called sample volume 5sv) that is volumetrically sampled by sensing member plurality 22mpl. Collectively, the plurality 22mp of deployed sensor members 22m or plurality 18pl of deployed resilient members 18 with coupled sensors 22 can comprise a 3 dimensional or volumetric sensor array 22a. By having sensors 22 in multiple locations and planes sensor array 22a is configured to volumetrically sample (e.g. sample in multiple locations) tissue within target tissue site 5' including tumor mass 5". Sensor array 22a is further configured to be able to simultaneously sample tissue at multiple locations within volume 5sv or tissue site 5' to perform one or more of the following: (i) locate the position of the tumor mass 5", (ii) discern the position or deployment distance of the energy delivery devices 18, (iii) monitor the developing ablation volume, (iv) perform tissue sensing biopsy and identification by comparing signals between two or more site (e.g. known healthy tissue and suspected diseased tissue). In various embodiments sensor array 22a and/or member plurality 18pl can be configured to define a variety of shapes for sample volumes 5sv including, but not limited to, a hemisphere, a sphere, an oval, a cone, pyramidal, a polyhedron or a tetrahedron.

Figure 3A:
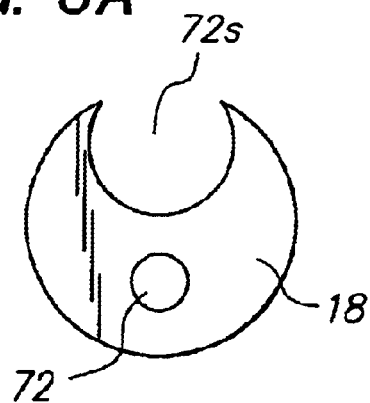
FIGS. 3a and 3b are cross sectional and perspective views illustrating embodiments of the resilient member having a slot.
Figure 3B:
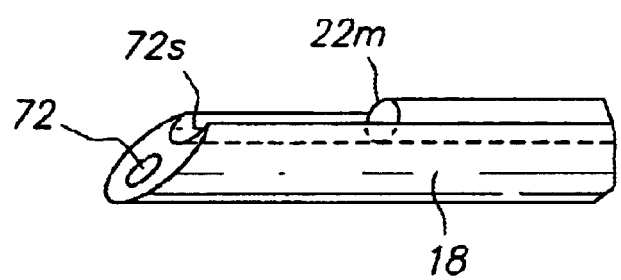
Figure 3C:
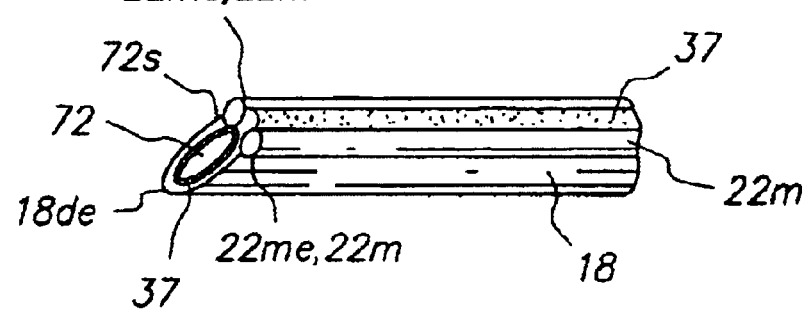
FIG. 3c is a perspective view illustrating an embodiment of the sensing member fixedly positioned to the resilient member.

Referring now to FIGS. 3a and 3b, in an alternative embodiment sensor member 22m can be advanced through a slot 72s in or on the surface of resilient member 18. Slot 72s serves as track to guide and advance sensor member 22m. Slot 72 also serves to increase the torsional flexibility of member 18 and to lesser extent lateral flexibility (the reciprocal of stiffness). The size and shape of slot 72s can also configured to increase the lateral flexibility of member 18 with a minimal affect on lateral flexibility (e.g. less than 10%). Shapes for slot 72s can include but are not limited to substantially semi-ovoid or semi-circular. In various embodiments the torsional flexibility of member 18 can be increased in the range of 10 to 200% with specific embodiments of 25, 50 and 100% with increases in lateral flexibility being lower in each case. Also in various embodiments, the torsional flexibility of member 18 can be controllably adjusted via the length of sensor member 22m positioned within slot 72s. In one embodiment member 18 with a slot 72 has a maximum flexibility when slot 72 is empty, as increasing lengths of sensor member 22m are advanced within slot 72 member 18 flexibility is decreased until sensor member 22m completely fills slot 72s. In a related embodiment shown in FIG. 3c, sensing members 22m can be fixedly attached to the exterior of resilient member 22 either in slot 72s or adhered to the surface of member 18 using an adhesive known in the art.

Figure 4:
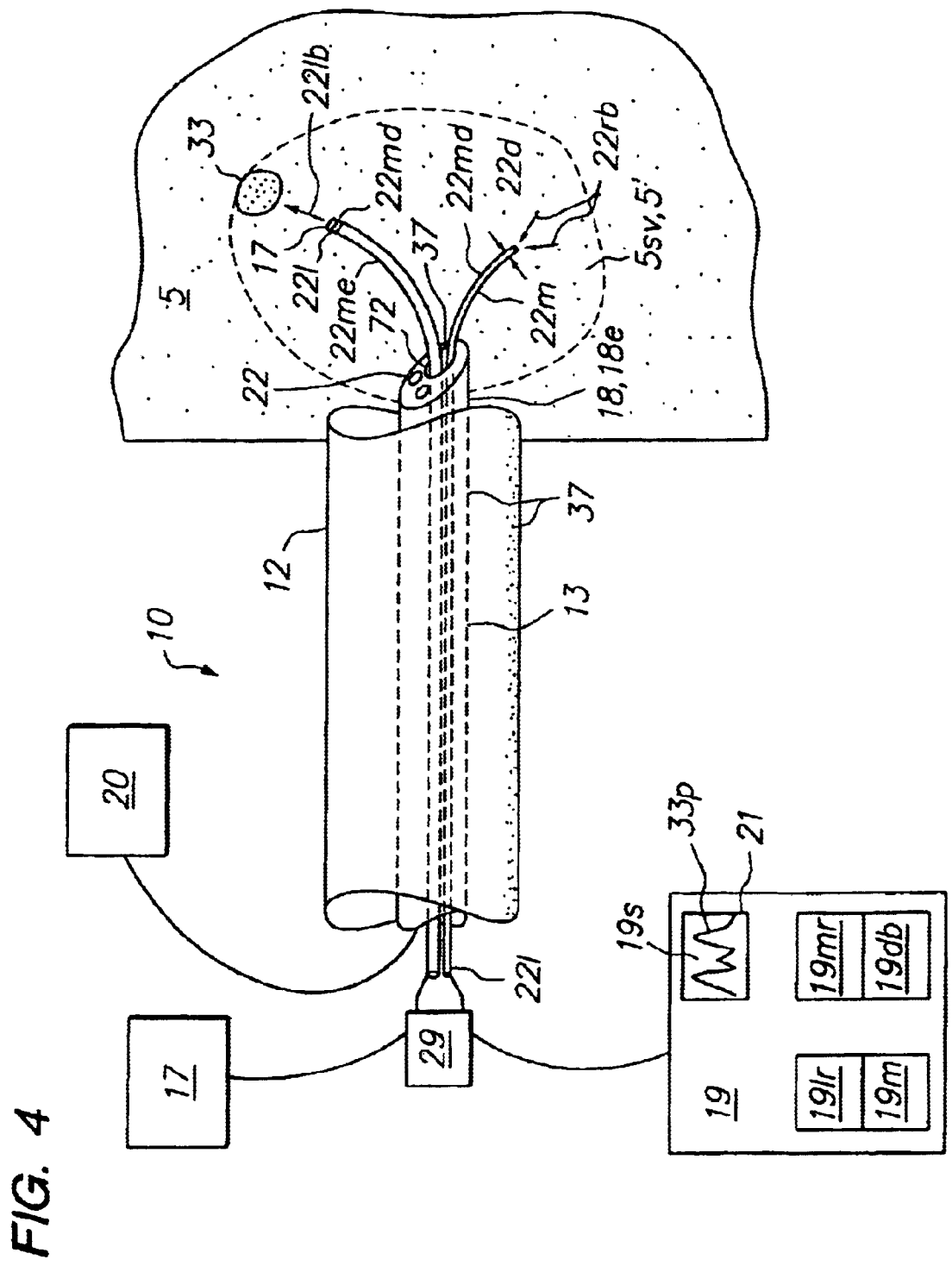
FIG. 4 is a perspective view illustrating an embodiment of a biopsy and treatment apparatus having an emitting member and detecting member positionable in the resilient member.
Figure 5:
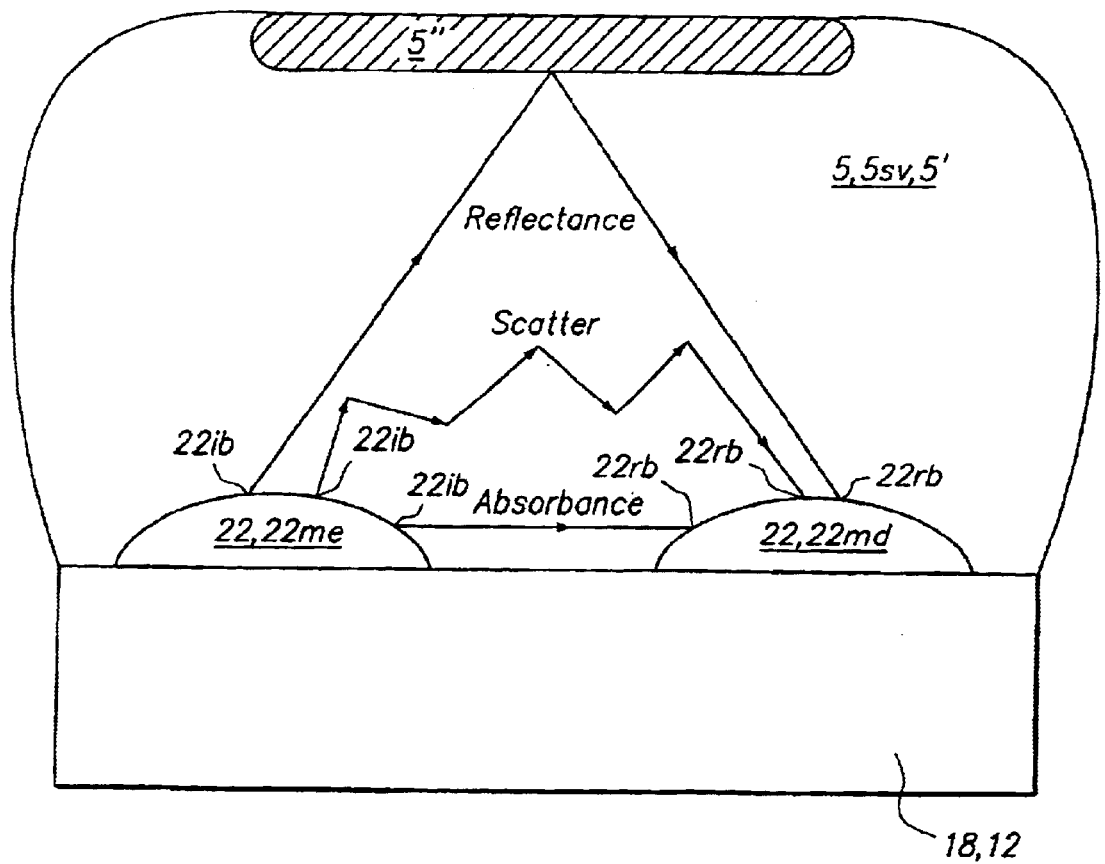
FIG. 5 is a schematic view illustrating various optical tissue interactions and properties.

In various embodiments, multiple sensing members 22m can be positioned and deployed from a single lumen 72 of resilient member 18 and/or from lumen 13 of introducer 12. Referring now to FIGS. 4 and 5, in an embodiment, two sensing members 22m can be positioned in a lumen 72 of one or more resilient members 18: a light emitting member 22me, configured to emit an incident or probe beam 22ib; and a light detecting member 22md, configured to detect returning light 22rb resulting from various optical tissue interactions (including scatter, reflectance or absorbance) of incident beam 22ib by tissue 5 as is shown in FIG. 5.

In these and other embodiments members 22m, 22me and 22md can be optical fibers including glass fiber known in the art such as those manufactured by the Dow Corning Corporation (Midland, Mich.) or Polymicro Technologies (Phoenix, Ariz.). The diameter 22d of fiber 22m can be in the range of 0.001 to 0.010" with a preferred embodiment of about 0.004" (without cladding). When light emitting member 22me is a fiber optic, one or more members 22me can include or be coupled (preferably at its distal end 22med) to a collimating or focusing lens 22l to collimate, and/or increase or decrease the size of incident beam 22ib. Similarly light detecting fiber 22md can include or be coupled to a collimating lens 22l preferably at the proximal end 22mdp of member 22 to collimate returning light prior 22rb prior to its entry into a optical measurement device described herein.

Figure 6:
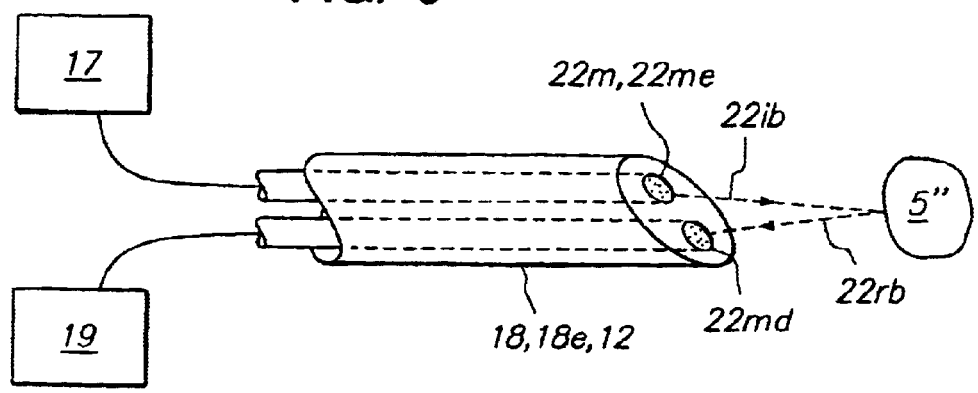
FIG. 6 is a perspective view illustrating an embodiment the sensing members fixedly positioned within the resilient member.

In an alternative embodiment shown in FIG. 6, sensing members 22 including emitting member 22me and detecting member 22md 22me can be fixedly positioned within resilient member 18 such that their distal ends are substantially flush with the distal end 18de of resilient member 18 or can fixed in other arrangements such as protruding slightly out of distal end 18de by several thousandths of inch or more or being recessed by a similar amount within distal end 18de. These embodiments provide the benefit of maintaining the optical relationship between the emitting and detecting members 22me and 22md constant, reducing signal variations due to movement of either member. In a related embodiment, sensing members 22me and 22me can also be fixedly positioned at or near the distal end 16 of introducer 12.

Sensing members 22 can be arranged in variety of configurations to perform one or more desired functions (e.g. tissue identification). Each resilient member 18 can have one or more sensing members 22. Some members 18 may have emitters 22me and some detectors 22md, so that selectable portions of tissue between members 18 can be interrogated via different optical paths. Emitters 22me and detectors 22md can be positioned anywhere within or outside of members 18 including at the tips 18de of members 18 where they can be fixedly positioned. Alternative embodiments may comprise emitters 22me and detectors 22md positioned on passive or otherwise non-energy delivery resilient members 18 so as to position at least some of the emitter and detectors beyond the developing or complete ablation volume 5sv. Such configurations allow for monitoring outside of tissue outside of the developing ablation volume to simultaneously compare un-ablated tissue 5 and ablated tissue 5av as well as reduce signal noise and artifacts from energy delivery within the ablation volume.

Referring back to FIGS. 2 and 4, in various embodiments one or more sensing member 22m can coupled to an optical switching device 29 or otherwise configured such that their function can be dynamically switched from an emitter to a detector mode and vice versa. By changing the optical function of sensing member 22m (e.g. from receiving to emitting) during the process of scanning or interrogating a desired tissue sample volume 5sv, directional biases, signal artifacts and detection errors can be reduced improving detection sensitivity. Further, different emitter detector combinations can be employed to obtain more accurate higher resolution signals and hence more detailed information about the target tissue. When both emitter member 22me and detecting member 22md are located in the same member 18, they can be operated simultaneously for localized tissue sampling and interrogation. Such configurations allow for the comparison of tissue adjacent one resilient member 18' to that of another resilient member 18". In a related embodiment, emitting or detecting sensing members 22 on multiple and/or distant resilient members 18 can be operated collectively to obtain a more global interrogation of a desired sample volume 5sv using one or more wavelengths.

Figure 7:
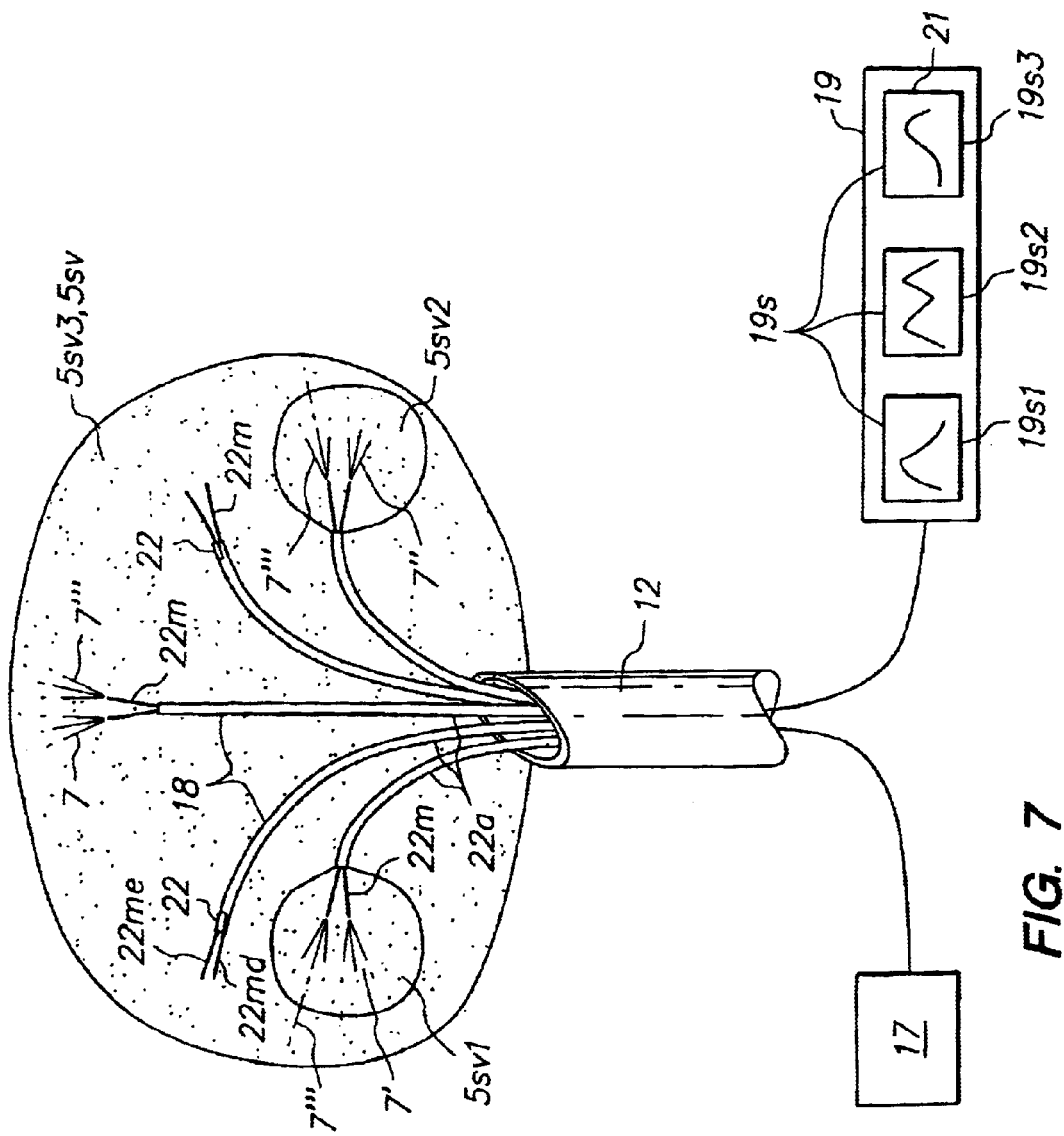
FIG. 7 is a perspective view illustrating the use of different wavelengths to sample multiple tissue volumes in an embodiment of the invention.
Figure 8A:
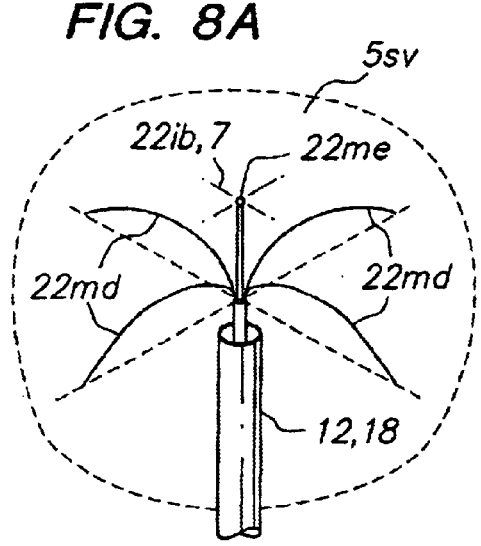
FIGS. 8a–8d are perspective views illustrating various arrangements of the emitting and detecting members.
Figure 8B:
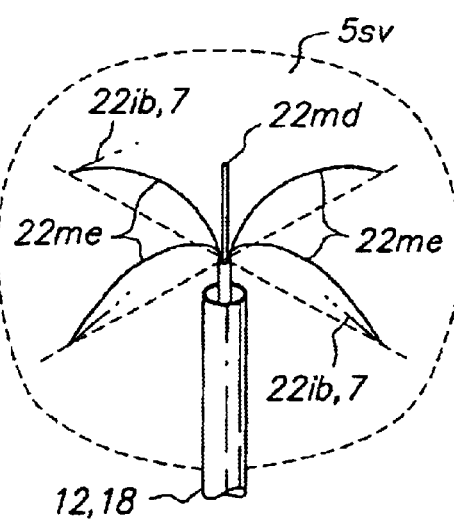
Figure 8C:
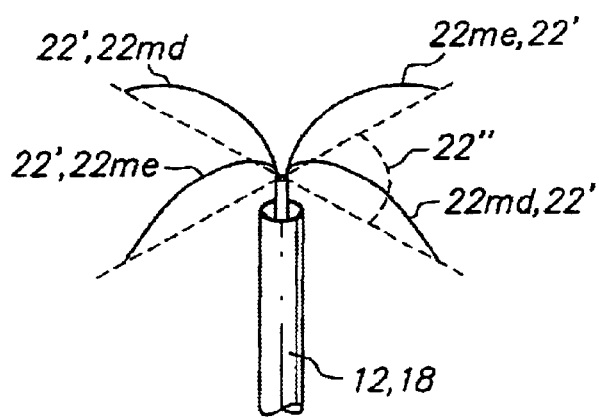
Figure 8D:
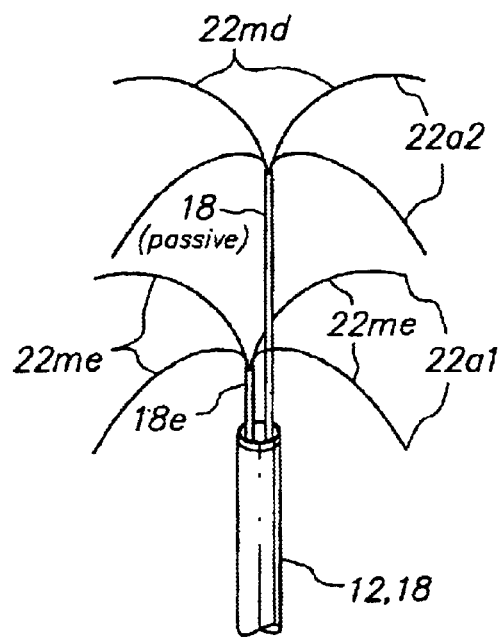

In various embodiments separate wavelengths can be used to simultaneously sample different locations within target tissue site 5'. In an embodiment shown in FIG. 7 a first interrogation wavelength or group of wavelengths 7' can be used to sample a local first volume 5sv1 and a second wavelength or group wavelengths 7" for a second volume 5sv2 and a third wavelength for larger or global sample volume 5sv3 defined or circumscribed by multiple sensor tipped members 18 or sensing members 22. Each sample volume 5sv probed with a given wavelength 7 results in a separate spectral profile 19s. Thus sample volumes 5sv1, 5sv2 and 5sv3 produce spectral profiles 19s1, 19s2 and 19s3 respectively.

Referring now to FIGS. 8a–8d, in various embodiments light emitting members 22me and light detecting members 22md can be arranged in arrays 22a having a variety of geometric arrangements and relationships so as to optically sample different volumes of tissue 5sv using different optical paths and/or optical tissue interactions. Such embodiments provide the benefit of improved acquisition, accuracy and analysis of the spectral signal 19s from a given sample volume 5sv to compensate for signal hysteresis, noise (due to energy delivery etc.) directional bias or other error. They also provide the benefit of simultaneous sampling and comparison of two or more tissue volumes to perform tissue identifications. In an embodiment shown in FIG. 8a, an emitting member 22me is positioned at the center of tissue volume 5sv with detecting members or sensor 22md positioned in a surrounding relationship so light passes from the center of the sample volume to the outlying sensors. In another embodiment shown in FIG. 8b, a detecting member 22md is positioned at the center of tissue volume 5sv with emitting members 22me or sensors 22 positioned in a surrounding relationship so as to transmit light inward. In yet another related embodiment shown in FIG. 8c, emitters 22m and detectors 22md can be located in a linear arrangements 22' that are substantially perpendicular or have another selectable angle 22". Alternatively as shown FIG. 8d, emitters 22me can comprise a first array 22a1 (such as perpendicular array) and the detector 22md located on a separate array 22a2. First array 22a1 can be rotated to obtain different optical paths to detector array 22a2 so as to sample different tissue volumes and/or provide multiple samplings of the same volume (via different optical paths) to improve accuracy and signal to noise ratios.

Figure 9:
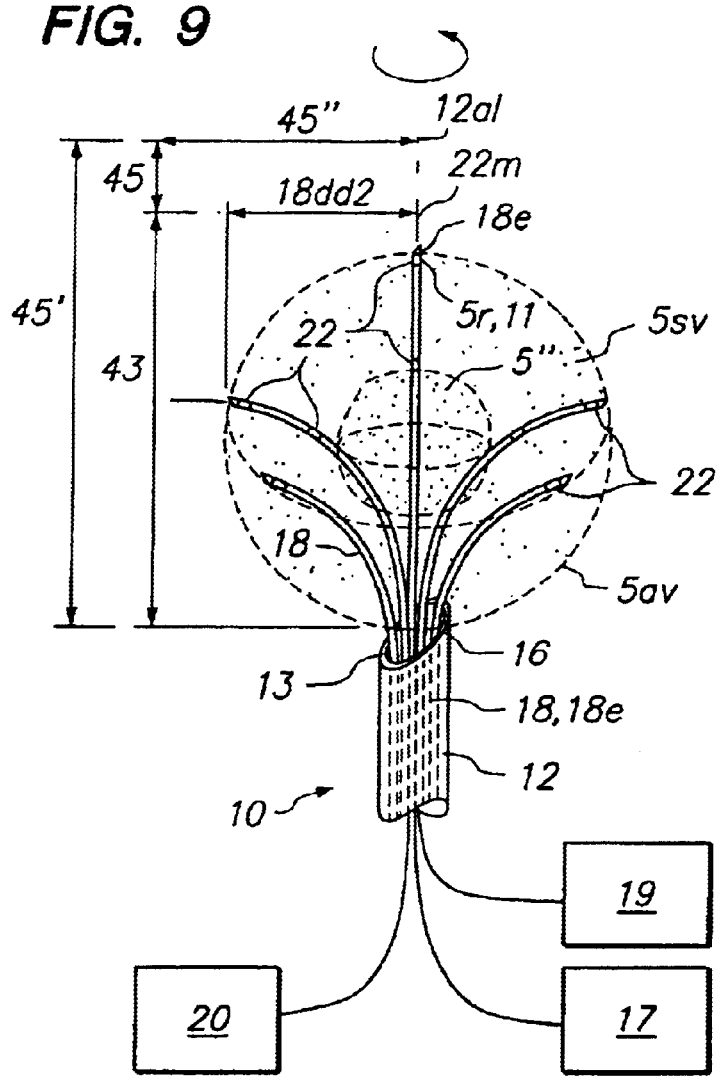
FIG. 9 is a perspective view illustrating an embodiment of a biopsy and treatment apparatus having sensors members positionable distally to the energy delivery member.

In another embodiment shown in FIG. 9, one or more sensor members 22m can be advanced from energy delivery member 18e so as to be positioned a selectable distance 45 distal to the distal end 18de of energy delivery member 18e (which corresponds to the deployment distance 43 of energy delivery member 18.). Distance 45 onto or even beyond the point that member 22m is positioned outside of the ablation volume 5sv. Distance 45 can be a greater longitudinal distance 45' or a lateral distance 45" with respect to a longitudinal axis 12a1 of introducer 12. This can also be achieved by the embodiment shown in FIG. 8d utilizing two or more arrays 22a, with at least one array positioned outside of the ablation volume.

Figure 10:
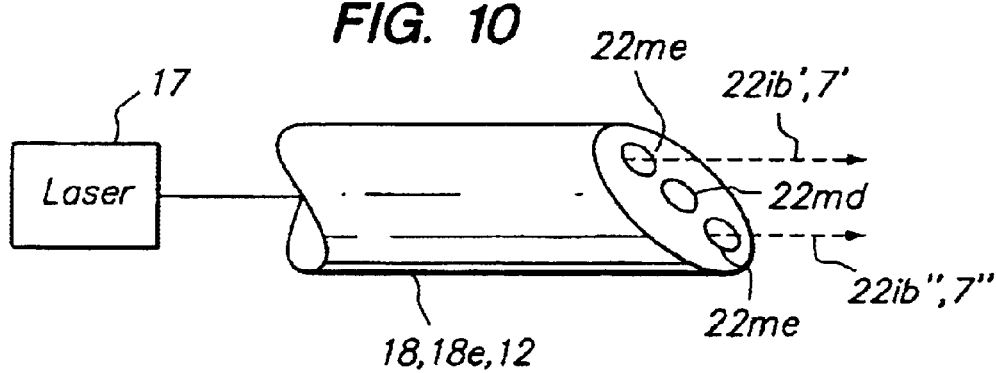
FIG. 10 is a perspective view illustrating an embodiment of the invention having a multiple wavelength laser light source.

Referring back to FIG. 4, emitting member 22me can include an integral light source 17 such as an LED or a diode laser or alternatively can be optically coupled to an external light source 17 which in various embodiments, can be configured to emit light at multiple wavelengths and over a range of wavelengths including, but limited to the range of 300 to 850 nm, a more preferred range of 450 to 850 nm with specific embodiments in the UV and infrared ranges. In an embodiment light source 17 can be a monochrometer known in the art. Examples of monochrometers include single crystal, double crystal and surface normal reflection monochrometers as well as models manufactured by Macken Instruments Inc. (Santa Rosa, Calif.). In other embodiments, light source 17 can be a white light source, a xenon bulb, an LED or a coherent light source such as a laser configured to emit probe beam 22ib. Examples of lasers include, but are not limited to, YAG lasers, Nd:YAG lasers, CO2 lasers, infrared lasers, argon lasers, tunable dye lasers and copper vapor lasers. Referring now to FIG. 10, laser device 17 can include multiple beams at different wavelengths including a first 22ib' and a second beam 22ib' having a first and second wavelength 7' and 7" wavelength. Examples of multiple wavelength emitting lasers include $CO_2$ lasers and argon-pumped tunable dye lasers. The use of multiple and/or a broad spectrum of wavelengths 7 provides the benefit of increased tissue or tissue chromophore specificity and hence increased predictive power (e.g. statistical confidence) of associated tissue identification algorithms described herein. The use of laser light source 17 with multiple beams and wavelengths can also be configured to determine the deployment distance of one or more members 18, 18e using laser range finding methods known in the art.

Referring back to FIG. 4, in an embodiment detecting member 22md can be coupled to an optical measurement device 19 such as a spectrophotometer, reflectometry device or CDC device. For ease of discussion, optical measurement device will now be referred to as a spectrophotometer, but all other embodiments are equally applicable. Spectrophotometer device 19 is configured to detect and record spectral information including a tissue spectra or spectral profile 19s resulting from optically induced tissue interactions such as reflectance, transmittance and scatter resulting from the incident light 22i from emitter 22me on tissue within sample volume 5sv.

In an embodiment, spectrophotometer device 19 can include logic resources 19lr such as a microprocessor and memory resources 19lr such as RAM or DRAM chip configured to analyze, store and display tissue spectral profile 19s and/or other optical information derived from sensing member 22m and/or sensing array 22a. Spectrophotometer device 19 can also be coupled to a display device 21 so as to display real time or stored spectra, images and other data generated by spectrophotometer device 19. Examples of display devices 22 include cathode ray tubes (CRTs), liquid crystal displays, plasma displays, flat panel displays and the like. Display device 22 can also be incorporated in an external computer 24 coupled to spectrophotometer device 19.

Figure 11:
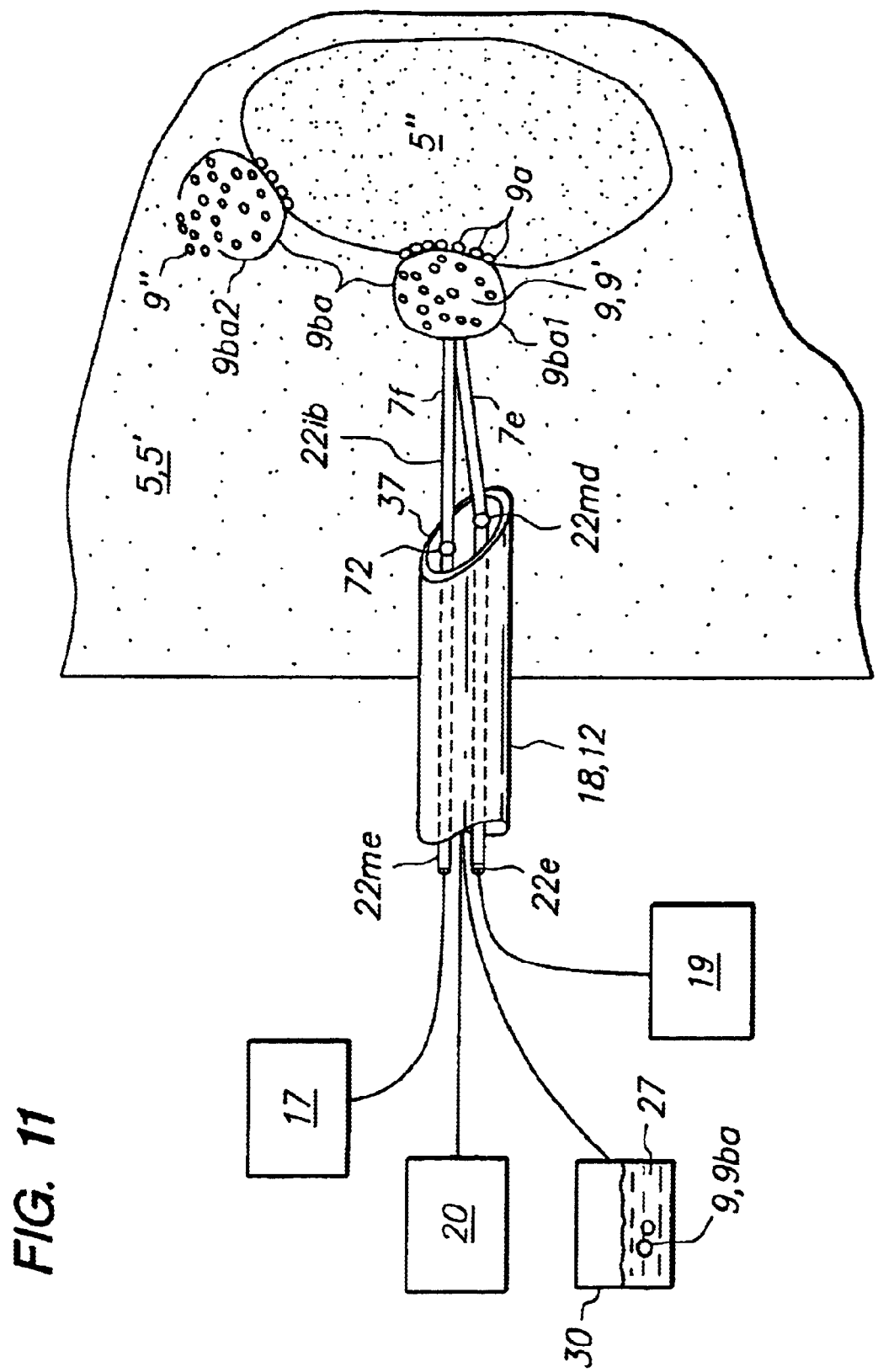
FIG. 11 is a perspective view illustrating use of an optical marker compound and binding agent in an embodiment of the invention.

Referring now to FIG. 11, in various embodiments light source 17 can also include a wavelength 7f configured to cause fluorescence of an optical marker compound or molecule 9 either naturally occurring or coupled to a tumor specific binding agent 9ba such as an antibody, protein or liposome known in the art. Antibody 9ba is configured to attach to a tumor specific antigen 9a. Binding agent 9ba can also be configure to be controllably release marker 9 when a specific tissue condition is met such as temperature, release of intracellular fluids/contents or other indications of cell lysis from ablative treatment. Binding agent 9ba can include a plurality of binding agents 9ba including a first and a second binding agents 9ba1, 9ba2 configured to be released a first and a second marker 9' and 9" upon a first tissue condition and a second tissue condition. An example of binding agent that is configured to controllably release a marker includes a liposome. Suitable liposomes include those manufactured by Liposome Technology Inc. (Menlo Park, Calif.). In various embodiments binding agents 9ba, 9ba1 or 9ba2 can be configured to release marker 9 in a temperature range from about 40° C. to about 60° C.; and more preferably in the range from about 45° C. to about 55° C. Marker 9 can also be configured to enhance the delivery of energy to tumor 5" and or increase the necrotic effect of energy on the tumor mass. An example of an energy delivery enhancing marker is a ferro-colloid compound.

In an embodiment, marker 9 and binding agent 9ba can be mixed in a solution 27 that is fluidically coupled to introducer 12 (via a reservoir or fluid delivery device described herein) and delivered to tissue site 5' through lumen 13 of introducer 12 or through lumen 72 of member 18.

In related embodiments, markers 9 can be configured to degrade upon a given tissue condition such that a decrease in the concentration of marker 9 serves as an indicator of that tissue condition, temperature being one example. In various embodiments, marker 9 can be configured to degrade or under a change in state or phase (e.g. solidify, liquefy or vaporize) upon a number of conditions or tissue treatments including: temperature or thermal irradiation, electrical current such as an RF current, ultrasound irradiation, UV radiation, ionizing irradiation and the like. These and related embodiments can be configured to be used in conjunction with an analytical method known in the art such as fluorescence spectroscopy described herein.

In various embodiments apparatus 10 and array 22a including members 22m can be configured to perform tissue identification, differentiation, ablation monitoring and mapping of tissue masses and structures. In specific embodiments, apparatus 10 is configured to perform a tissue biopsy function using optical or other information derived from array 22a. Such information is obtained by probing the target tissue volume 5sv with an incident beam 22ib having one or more wavelengths 7. As described herein, the optical tissue interactions of incident beam 22ib on target tissue site 5' result in a distinct spectral profile 19s that serves as a fingerprint of the tissue type. As shown in FIG. 5 the main optical tissue interactions include scatter, reflection and absorption and to a lesser extent fluorescence.

Referring back to FIG. 4, these optical tissue interactions are controlled to a large extent by chromophores 33 that result in one or more peaks 33p within profile 19s. Chromophores 33 can include metabolic chromophores 33 that are individually or collectively predictive of a particular tissue type including cancerous tissue. By analyzing and matching peaks 33p corresponding to one or more of these chromophores 33, spectral profile 19s has predictive value for tissue type and/or a tissue condition such as necrosis or thermal injury. Further, many tissue types will have a signature profile 19s that can be readily identified and matched to a database of profiles using pattern recognition techniques or algorithms known in the art including fuzzy logic methods. Accordingly, apparatus 10 including sensor array 22a can be configured to generate and analyze a composite spectral profile 19s including reflectance, absorption and fluorescence components depending on the tissue type and associated chromophores of interest. Alternatively, apparatus 10 can sensor array 22a can be configured to generate and analyze individual spectral profiles 19s for a particular optical property, again depending on the chromophores of interest.

Referring still to FIG. 4, in various embodiments, apparatus 10 can include electronic algorithms or software modules 19m resident in logic resources 19lr of device 19 or microprocessor 339 that are configured to analyze profile 19s and perform tissue identification and/or tissue differentiation between one or more sampled volumes 5sv. Modules 19m can include pattern recognition algorithms or fuzz logic. Also in an embodiment, modules 19m can be configured to compare profile 19s to a database of profiles 19db stored in memory resources 19mr use curve fitting or other numerical methods known in the art to provide and display a correlation coefficient or statistic indicative of the probability of a match to a particular tissue type.

Figure 12:
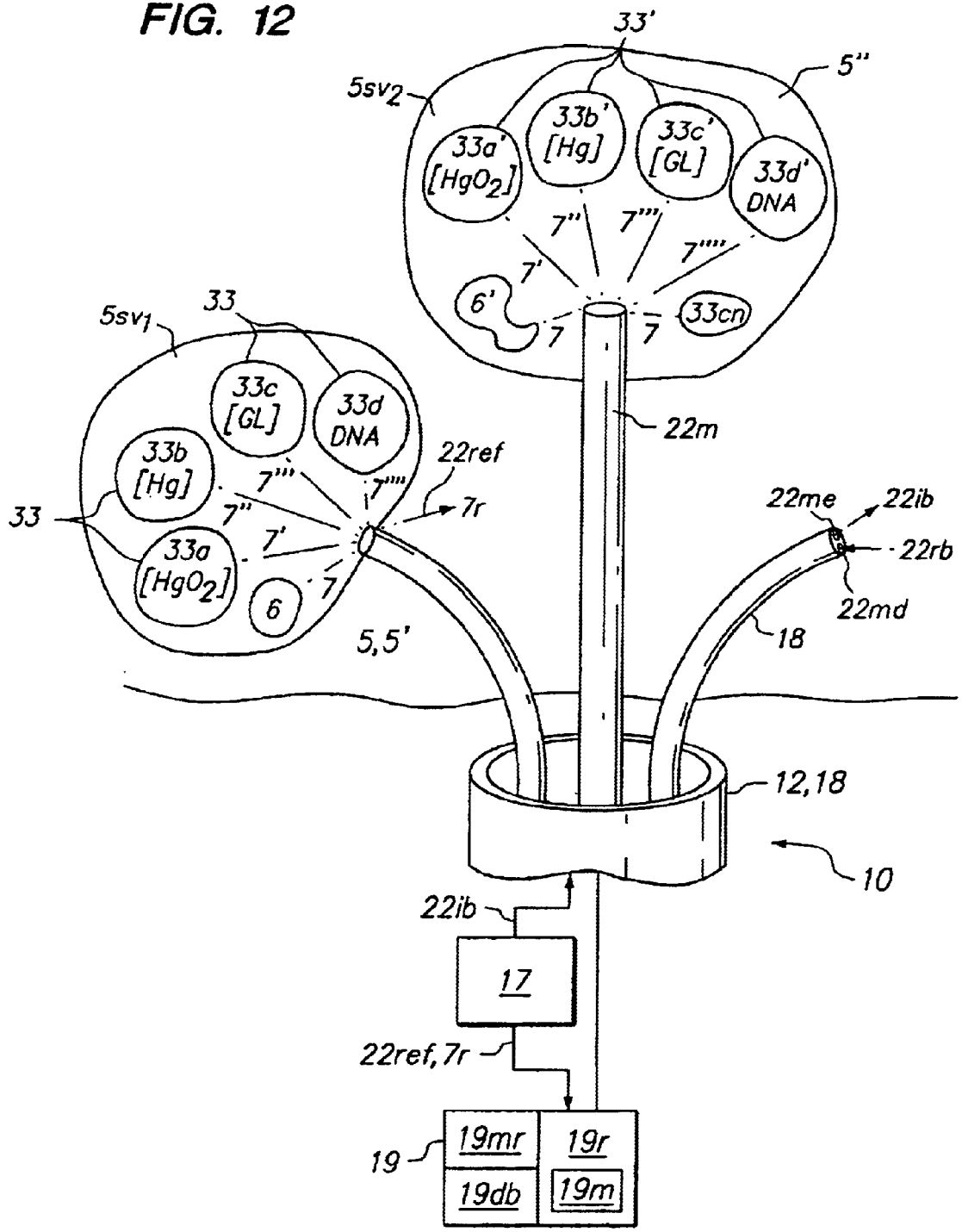
FIG. 12 is a perspective view illustrating an embodiment of a biopsy and treatment apparatus configured to detect metabolic chromophores.

Referring now to FIG. 12, in various embodiments apparatus 10 can also be configured to differentiate cancerous or other abnormal tissue vs. healthy tissue based on metabolic abnormalities of cancerous tissue. Accordingly in various embodiment, apparatus 10 and arrays 22a can also be configured to detect and/or quantify specific chromophores 33 including metabolic chromophores 33, also called metabolites 33 that are predictive or otherwise indicative of cancerous tissue, precancerous tissue, abnormal tissue, necrosed tissue or injured tissue. In an embodiment, apparatus 10 can be configured to detect and/or quantify a plurality of metabolites 33p that can include a first, second, third and fourth metabolite, 33a, 33b, 33c, and 33d. Software module 19a can compare detected metabolite concentrations for one or mores of these metabolites to a database of 19dp of metabolite concentrations for known cancer types and use curve fitting, fuzzy logic or other numerical methods to establish a match along with an associated confidence metric such as a p-value. In an alternative embodiment, apparatus 10 including module 19a can be configured to utilize relative differences in concentrations of metabolites 33 by detecting and measuring concentrations of metabolites in a first sample volume 5sv1 containing healthy tissue can compare those to measurements for cancer metabolites 33' of a second sample volume 5sv2 believed to be a tumor or cancerous tissue volume 5". Module 19m can calculate the differences and compare one or more of them to a database 19db of differences for known cancer types and use curve fitting, fuzzy logic other numerical methods to establish a match along with an associated confidence metric.

In a related embodiment, emitter 22me can also be configured to emit a reference beam 22ref at a reference wavelength 7r that does not appreciably interact with the target chromophore 33 so as to compensate for tissue hysteresis. In another related embodiment spectrophotometry device 19 can be a dual beam spectrophotometer in which a reference beam 22ref is also used to compensate for any hysteresis in the light source 17.

In various embodiments, predictive metabolites 33 include, but are not limited to, oxyhemoglobin, deoxyhemoglobin DNA and DNA fragments, tissue oxygen or $PO_2$, lipids, glucose, acids, $CO_2$, sodium, potassium, calcium and intracellular fluid and the like. This can be achieved by probing the tissue with wavelengths of incident light 22ib known to be absorbed or cause fluorescence of these chromophores. Oxyhemoglobin has strong absorption bands in the visible spectrum with the strongest absorption peak of occurring at 418 nm. Two additional absorption peaks with lower absorption coefficients occur at 542 and 577 nm. Glucose is known to absorb in the near infrared range. Two other cancer predictive chromophores 33' include NAD(P)H and flavins that fluoresce in the ultra-violet and near ultra-violet range.

Differences in the concentration of metabolites 33 for healthy tissue verses metabolites for cancerous tissue 33' result from the metabolic differences of cancerous tissue. A discussion will now be presented of those differences. Since many cancer or tumors are over vascularized relative to normal tissue a higher total amount of oxyhemoglobin in a given sample volume of tissue can indicate cancer. At the same time, since cancer cells are more rapidly dividing and have higher metabolic rate than normal tissue the tumor will typically be slightly hypoxic and thus have lower $PO_2$ levels and or oxyhemoglobin concentrations (or higher deoxyhemoglobin concentrations) relative to normal tissue. Also, owing to higher metabolic rates, tumors will frequently have lower interstitial glucose concentrations and higher $PCO_2$ levels as well as lower pH which sensor array 22a can be configured to detect. Further, as described herein, tumors will have different (usually higher) rates of DNA synthesis as well as abnormal DNA one or both of which can be detected by sensor array 22a using DNA probe methods.

In one embodiment of an optical biopsy method, fluorescence spectroscopy can be employed for optical biopsy including tissue identification and ablation monitoring. In this method, the wavelength 7 of the incident beam 22ib is altered by interaction with the target tissue resulting in an emitted or returning light 22rb at a different wavelength known as the emitted wavelength 7e. Sampling and analysis of the emitted light by detection member 22md and coupled spectrometer device 17 (which in this embodiment is a UV spectrometer) results in the generation of a fluorescence emission spectrum 19s. This is a plot of the intensity of emitted fluorescent light as a function of emission wavelength produced when the target tissue is illuminated at a particular wavelength 7f. Spectra 19s is then compared matched to and to database 19db of UV spectra for known cancer types or cancer predictive metabolites 33'.

In other embodiments apparatus 10 and sensor array 22a can be configured to detect and quantify metabolic chromophores or metabolites 33cn indicative of cell necrosis, injury or ablation. These metabolites result from various cellular functions occurring during cell necrosis. More specifically, when cells are heated by ablation treatment such as RF energy they heat to the point where their proteins are denatured, cell walls rupture and their contents released which includes a number of necrotic indicating metabolites 33cn. Such necrotic indicating metabolites 33cn can include but are not limited to collagen, denatured collagen, fatty acids, lipids, cell membrane lipids, billirubin, and vapor bubbles and carbonized tissue. In a related embodiment, sensor array 22a can also be configured to monitor for decreases in metabolic chromophores 33 resulting from thermal or other ablative treatment. For example, decreases in hemoglobin due its thermal breakdown result in a tissue color e.g. from red to white which can be readily detected by sensor array 22a for portions or an entire target tissue site 5'. Besides hemoglobin, other decreasing chromophore 33 concentrations that can be monitored as indicators for cell necrosis include myoglobin, collagen and melanin.

In alternative embodiments, sensor array 22a including members 22m, 22me and 22md can be configured to detect and distinguish between normal cells 6 and abnormal cells 6' including abnormal cell shapes, sizes and morphology as a means of identifying cancerous, precancerous or other abnormal tissue. This can be accomplished using a variety of optical cell sorting and optical particle sizing techniques known in the art including fluorescence tagging methods. Cancer cells 6' will frequently be drastically different from a normal cell 6 including being larger, having a larger more dense nucleus and being irregularly shaped. Array 22a can be configured to detect one or more of these abnormalities and input them to logic resources 19. There modules 19m can be configured to compare these abnormalities to a database 19db of known abnormalities and make a tissue identification based on pattern recognition or fuzzy logic algorithms which can be similar to those used for finger print identification.

Figure 13:
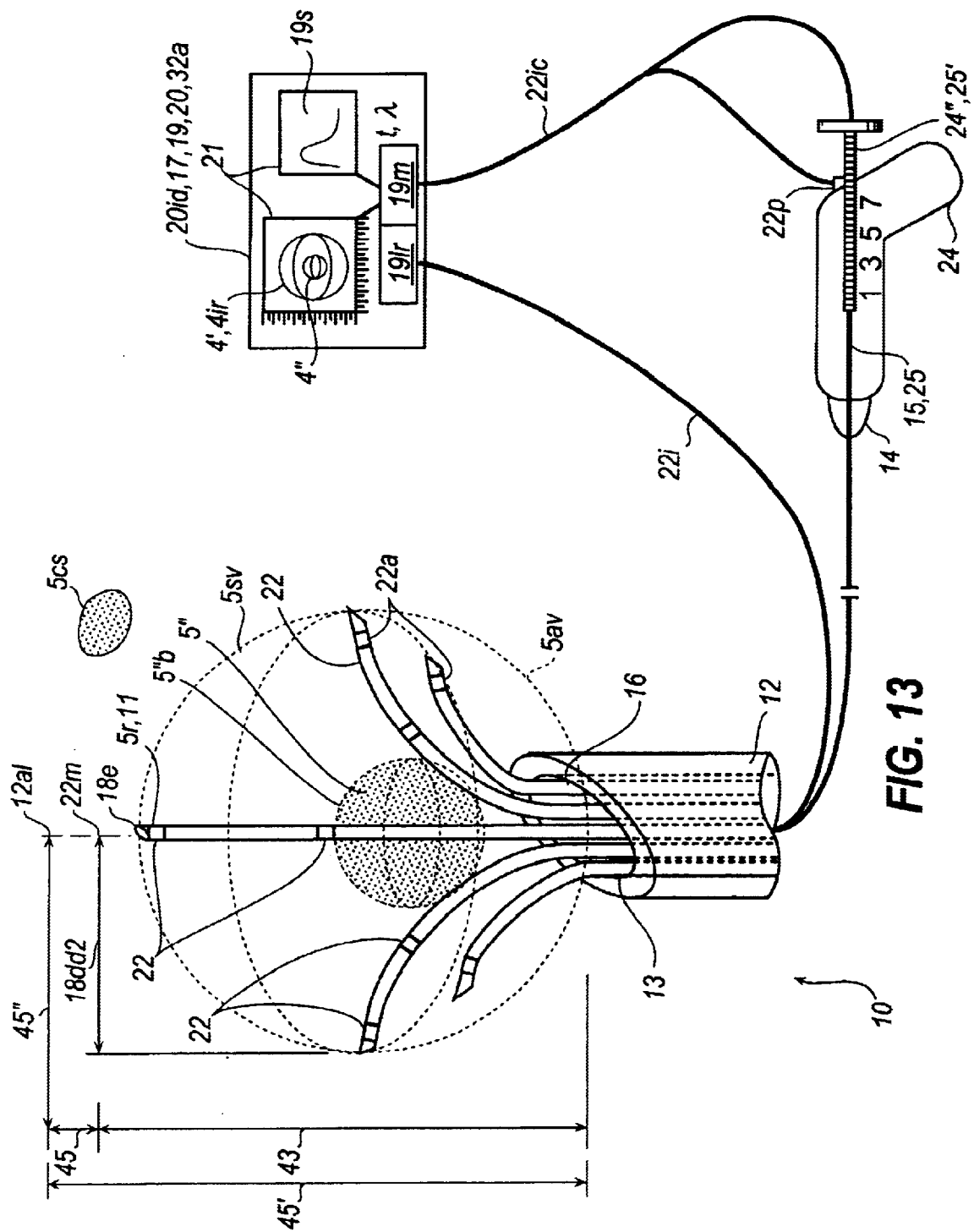
FIG. 13 is a perspective view illustrating an embodiment of a biopsy and treatment apparatus configured to generate a 3D map of the tumor.

In various embodiments apparatus 10 and sensor array 22a can be configured to optically probe tissue site 5' and generate an image or map of the tumor volume and other structures within the target tissue site 5'. In an embodiment shown in FIG. 13, apparatus 10 and sensor array 20a are configured to probe/scan the tissue volume 5" simultaneously in 3 dimensions (e.g. volumetrically sample) to determine the border 5"b of tumor mass 5" so as to locate and map the tumor mass 5" in 3 dimensions. The process can be facilitated by having one or more known reference points 5r on members 18 that are determined via a positional sensor 22p on deployment device 24" that is configured to determine deployment distance 43 of a selected member 18e. (reference point 5r can also be a radiopaque marker 11 positioned at set distance along member 18e). The mapping process can also be facilitated by rotating array 22a about introducer axis 12al or advancing and retracting one or more sensing members 22m from members 18 or a combination of both. Signals 22i from sensor array 22a as well those from position sensor 22p can then be input to logic resources 19lr where module 19m generates a 3 dimensional map 4" of the tumor volume using one or more image processing algorithms known in the art including, but not limited to, edge detection (to define tumor boundary 5"B), filtering, volume imaging, contrast enhancement and fuzzy image processing algorithms and the like. Module 19m can then be configured to display map 4" on a coupled display device 21 (using volume image display algorithms such as numeric projection). The generation of 3D map 4" allows the user to accurately position energy delivery members 18e within tumor mass 5" while establishing the position of and avoiding nearby critical anatomical structures 5cs. Further, the volumetric sampling and 3D mapping capability of embodiments of the invention solves the shortcomings of 2D intra-operative imaging methods including poor resolution of the tumor mass, difficulty in visualization of the tumor volume including misjudgment of the size, shape and location of the tumor volume. In related embodiments detectors 22me can be configured to monitor in the near infrared range to produce an infrared/thermal image 4ir of sample volume 5sv that can include tumor mass 5" or ablation volume 5av.

Figure 14A:
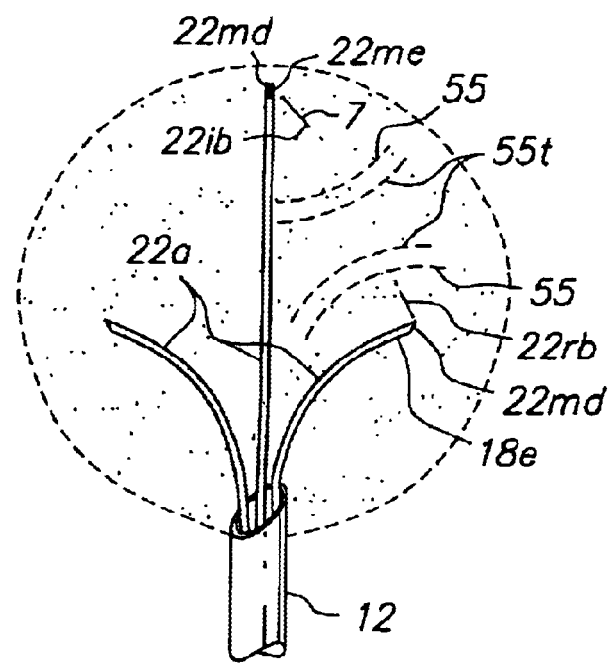
FIG. 14a is a perspective view illustrating use of sensor array to monitor a developing ablation volume.
Figure 14B:
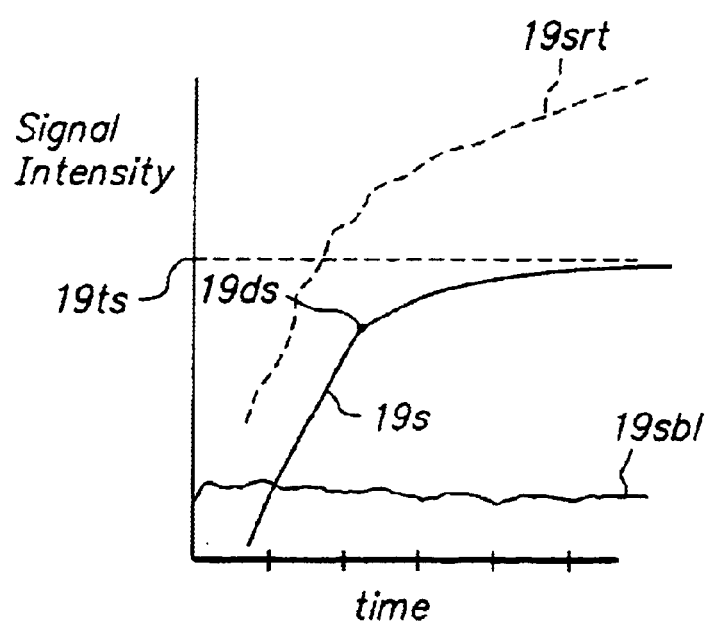
FIG. 14b is a plot of spectral signal intensity verses time for a sample volume of ablating tissue illustrating quantitative determinants of an ablation endpoint.

In addition to identifying tissue types, apparatus 10 and sensor arrays 22a can also be employed to monitor the progression of an ablative procedure including the progression of an ablation volume 5av resulting from the delivery of energy to target tissue volume 5. Referring now to FIGS. 14a and 14b, emitters 22a and detectors 22md can be configured to monitor the moving boundary layer of cell necrosis 55 and/or thermal fronts 55t of a developing ablation volume 5av. This can be achieved by monitoring for the presence of metabolic chromophores 33 or markers 9 indicative of cell necrosis or ablation described herein. The spectral signal intensity 19s (at one or more wave lengths 7) for a volume of tissue between one or more emitters 22me and detector 22md can be monitored over time. An endpoint for ablation can be determined based on either a selectable threshold value 19ts of signal 19s or an inflection point or change in slope 19ds (e.g. a derivative) of curve 19s or a combination of both. In an embodiment signal 19s can comprise the subtraction of a baseline (or reference) spectral measurement 19sbl of a nearby, but non-ablated tissue volume, from a real time measurement 19srt of the target tissue volume during the time course of ablation. This compensates for any signal or tissue hysteresis over time. Signal/curve 19s can include both spectral, thermal and impedance measurements. Values for 19ts and 19s can be input and stored in logic resource 19lr coupled to spectrophotometer 19 or incorporated into an electronic algorithm controlling the delivery of energy which can be stored in a controller or processor 338 coupled to power supply 20.

In related embodiments, sensor array 22a can be configured to monitor for any number of indicators of cell necrosis that can be utilized to qualitatively or quantitatively assess the progress of an ablation and determine a meaningful clinical endpoint. Such indicators and associated monitoring and endpoint methods include, but are not limited to, the following: monitoring interstitial moisture or hydration levels (these would be expected to go up as cells lyse and then go down as fluid is boiled or evaporated) and utilizing a decrease below a lower threshold as an endpoint; monitoring interstitial electrolyte concentrations (which increase with cell lysis): monitoring for interstitial fatty acid and amino acid concentrations (which would increase with cell lysis and then decrease due thermal degradation); monitoring for the increase or decrease of marker compounds 9; monitoring impedance; monitoring tissue temperature changes using near-infrared or thermocouple measurements; monitoring tissue color changes (e.g. red to white), monitoring for protein or collagen denaturization; monitoring for the release of DNA, gene fragments, DNA fragments or degraded DNA; monitoring for the release of RNA, RNA fragments or RNA fragments; monitoring for changes in tissue oxygenation in the form of $PO_2$ or oxyhemoglobin; monitoring for changes in $PCO_2$; monitoring for decrease or cessation of blood flow rates (an indication of tissue coagulation) using optical (e.g. laser Doppler) or acoustical (e.g. doppler ultrasound) sensors and monitoring for the presence of vapor bubbles and rate of vapor bubble formation. In a specific embodiment, sensor array is configured to monitor the rate of vapor bubble formation (using either optical and/or acoustic/ultrasound sensors 22) and as an indicator of both rate of ablation and also a treatment endpoint. A treatment control and endpoint algorithm in module 19a employing this method would initially look for an increase in bubble rate formation and then a decrease below a set threshold as the endpoint. Other related embodiments can be configured to monitor for various cellular functions indicative of injury or necrosis.

The target tissue site 5" can also be probed and interrogated by sensor array 22a after the completion of ablation to confirm that ablation is complete for the entire desired volume ablation volume. By probing the ablated region with sensor array 22, the 3 dimensional volume of the ablation can be assessed and the margin 5 m of ablated healthy tissue beyond the tumor mass 5" can also be measured.

Figure 15:
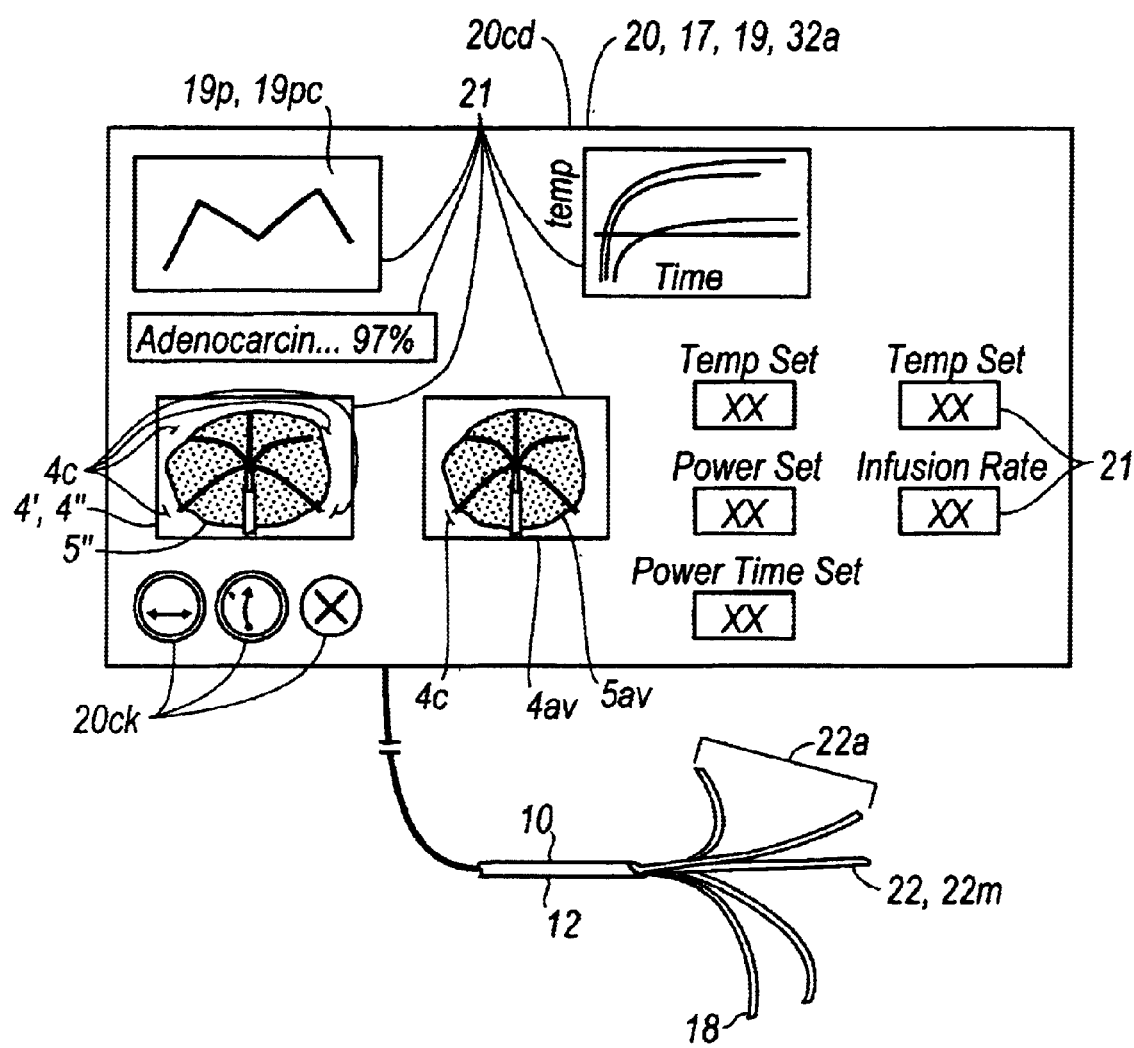
FIG. 15 is a lateral view illustrating a control and display unit used in various embodiments of the invention.

Referring now to FIG. 15, in an embodiment power supply 20, display device 21, controller 329 and/or light source 17 and/or optical device 19 can be incorporated or integrated into a single control and display device or unit 20cd. Device 20cs can configured to include display one or more of the following: spectral profile 19s, tissue site image 4', tumor volume image 4", ablation volume image 4av, time temperature profiles, tissue identification information, and ablation setting information (e.g. power setting, delivery time etc.). Device 20ed can also be configured to superimpose ablation volume image 4av onto tumor volume image 4" or tissue site image 4' as well as superimpose visual cues 4c on the placement (including proper and improper placement) of apparatus 10 including energy delivery devices 18e within the tumor volume 5" or tissue site 5". Device 20cd can also include controls knobs 20ck for manipulating any of the images (4', 4" or 4av) in one or more axis.

Referring now to FIGS. 16a–16c, in an embodiment of a method of the invention sensor array 22a can be utilized to ensure proper placement of energy delivery member 18e to achieve the desired ablation volume 5av as well as detect various improper placements. Referring to FIG. 16a, as energy delivery members 18e are advanced out of introducer 12 sensors 22 positioned at distal tip 18de or sensor members 22/array 22a can be utilized to locate and map tumor mass 5", sense the position of energy delivery members 18e relative to the tumor mass and determine an ablation volume 5av based on the current position of members 18e. As shown in FIG. 16a, sensors 22 or members 22 can be used to determine and alert the user when one or more energy delivery members are positioned outside of tumor mass 5" and/or when the resulting ablation volume 5av would not encompass the entire tumor mass 5". Device 20cd or other coupled monitoring device can then be configured to alert the use of the necessity of repositioning one or more energy delivery members 18e providing visual cues as to which member to move and by how much distance. Referring now to FIG. 16b, as members 18e continue to be advanced into the tumor volume mass sensors 22 or members 22 can also determine if members 18e not positioned properly to produce an ablation volume 5av that has an adequate healthy tissue margin 5 m with respect to tumor mass 5". Again, the user could be alerted of the need to reposition one or more member 18e. Referring now FIG. 16c, as members 18e continue to be advanced sensors 22 or member 22 can be configured to determine when members 18 are properly positioned to produce the desired ablation volume 5av, the user being subsequently alerted by device 20cd.

Referring now to FIGS. 17a and 17b, in other method embodiments of the invention sensors 20 or sensor array 22a can be utilized to detect incomplete ablation volumes. In the embodiment shown in FIG. 17a, one or more members 18e with coupled sensors 22 or sensor members 22m can be rotated about the introducer axis 12 to move the array members 22m from a first array position 22a' defining a first sample volume 5sv1 to a second array position 22a" defining a second sample volume 5sv2 so as to detect areas of incomplete ablation that are outside of the plane defined by two or more energy delivery members 18e. By rotating introducer 12 or members 18, array 22a can be rotated about axis 12al in any desired amount from 1 to 360° to sample any desired tissue volume and ascertain that the entire tumor volume 5" has been ablated along with the desire amount of healthy tissue margin 5 m. In another embodiment shown in FIG. 17b, incomplete ablation can be determined by advancing sensor members 22m or passive members 18 with coupled sensors 22 outside of the immediate area or volume 5ev defined by energy delivery members 18e and interrogating a desired tissue volume with sensors 22 or member 22m to determine if it has been sufficiently ablated. This procedure can be repeated with sensor members 22m or member 18 being further advanced with subsequent tissue interrogations until sensors members 22m or sensors 22 are positioned at the border 5av' of the desired ablation volume 5av and a determination has been made that all sampled tissue has been adequately ablated.

Figure 18A:
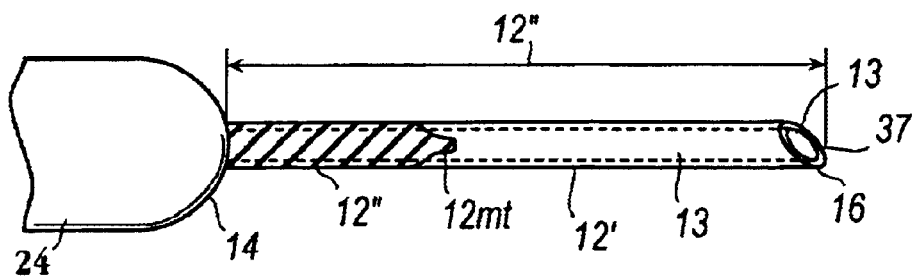
FIG. 18a is a lateral view illustrating the configuration of the introducer.

Turning now to a further discussion of introducer 12, in various embodiments, introducer 12 can be a trocar, catheter, multi-lumen catheter, or a wire-reinforced or metal-braided polymer shaft, a port device, a subcutaneous port device or other medical introducing device known to those skilled in the art. In various embodiments, introducer 12 as well as resilient member 18 can be configured to have varying mechanical properties along their respective lengths including, but not limited to variable stiffness, torquability, bendability, flexural modulus, pushability, trackability and other mechanical performance parameters known in the catheter arts. Referring to FIG. 18a, this can be achieved through the use of stiff shafts sections 12''' disposed within portions of introducer 12 along its length 12''. It can also be accomplished through the use of braids, varying/tapered diameters and different materials (e.g. stiffer materials joined to flexible materials) positioned over portions of introducer 12. Sections 12''' made from different materials can be joined using introducer bonding methods known in the art such as hot melt junctions (with and without capture tubes/collates), adhesive joints, but joints and the like. The joining method can be controlled/selected so as to control the mechanical transition 12mt between two sections to a desired gradient (e.g. smooth vs. abrupt). In related embodiments, introducer 12 and/or member 18 can be configured to have stiffer proximal portions and more flexible distal portions so as to facilitate one or more of the following (i) introducer steerability and positioning of distal tip 16 at a selectable target tissue site 5', (ii) reduced risk of perforation, abrasion and other trauma during the positioning the introducer to the tissue site. In various embodiments, the transition from the stiffer to the more flexible portion can be configured to be either (i) gradual with a linear or curve-linear transition, (ii) a step or abrupt transition, and (iii) combinations thereof.

Figure 18B:
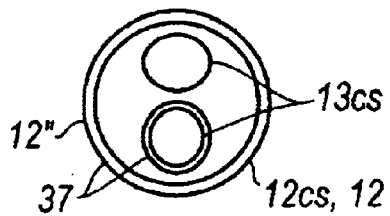
FIGS. 18b and 18c are cross sectional views illustrating cross-sectional profiles of the introducer.
Figure 18C:
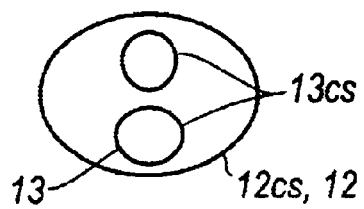
Figure 19:
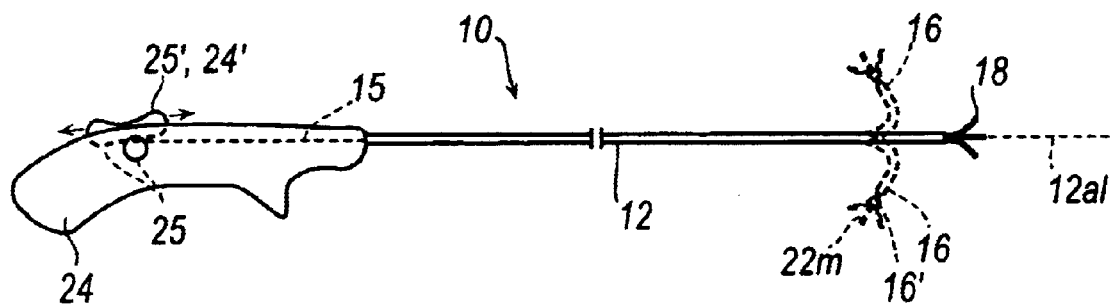
FIG. 19 is a lateral view illustrating an embodiment of a deflectable introducer along with the components of the introducer.

Referring to FIGS. 18b and 18c, introducer 12 can have a substantially circular, semicircular, oval or crescent shaped cross sectional profile 12cs, as well as combinations thereof along its length. Similarly, lumens 13 can have a circular, semicircular, oval or crescent shaped cross section for all or a portion of the 12' length of introducer 12.

Suitable materials for introducer 12 and resilient member 18 include, but are not limited to, stainless steel, shape memory alloys such as nickel titanium alloys, polyesters, polyethylenes, polyurethanes, Pebax®, polyimides, nylons, copolymers thereof and other medical plastics known to those skilled in the art. All or portions of introducer 12 can be coated with a lubricious coating or film 12' which reduces the friction (and hence trauma) of introducer 12 with hepatic, pulmonary, bone and other tissue. Such coatings can include but are not limited to silicones, PTFE (including Teflon®) and other coatings known in the art. In a related embodiment introducer 12 and member 18 can have an optical coating 37 on their exterior surface or within lumens 13 or 72 that is configured to reduce reflection or glare from their respective surfaces that may cause false optical signals or otherwise interfere with the optical sampling process by sensing members 22. Optical coating 37 can be any non-reflective, glare resistant coating known in the art or can be a surface treatment such as anodization.

Also, all or portions of apparatus 10 including introducer 12 and members 18 can be constructed of materials known in the art that are optimized and/or compatible with radiation sterilizations (e.g. Gamma or E-beam). In related embodiments, all or portions of apparatus 10 can be configured (e.g. lumen diameter to length ratio, etc) to be sterilized by plasma (e.g. $H_2O_2$) sterilization by systems.

Figure 20:
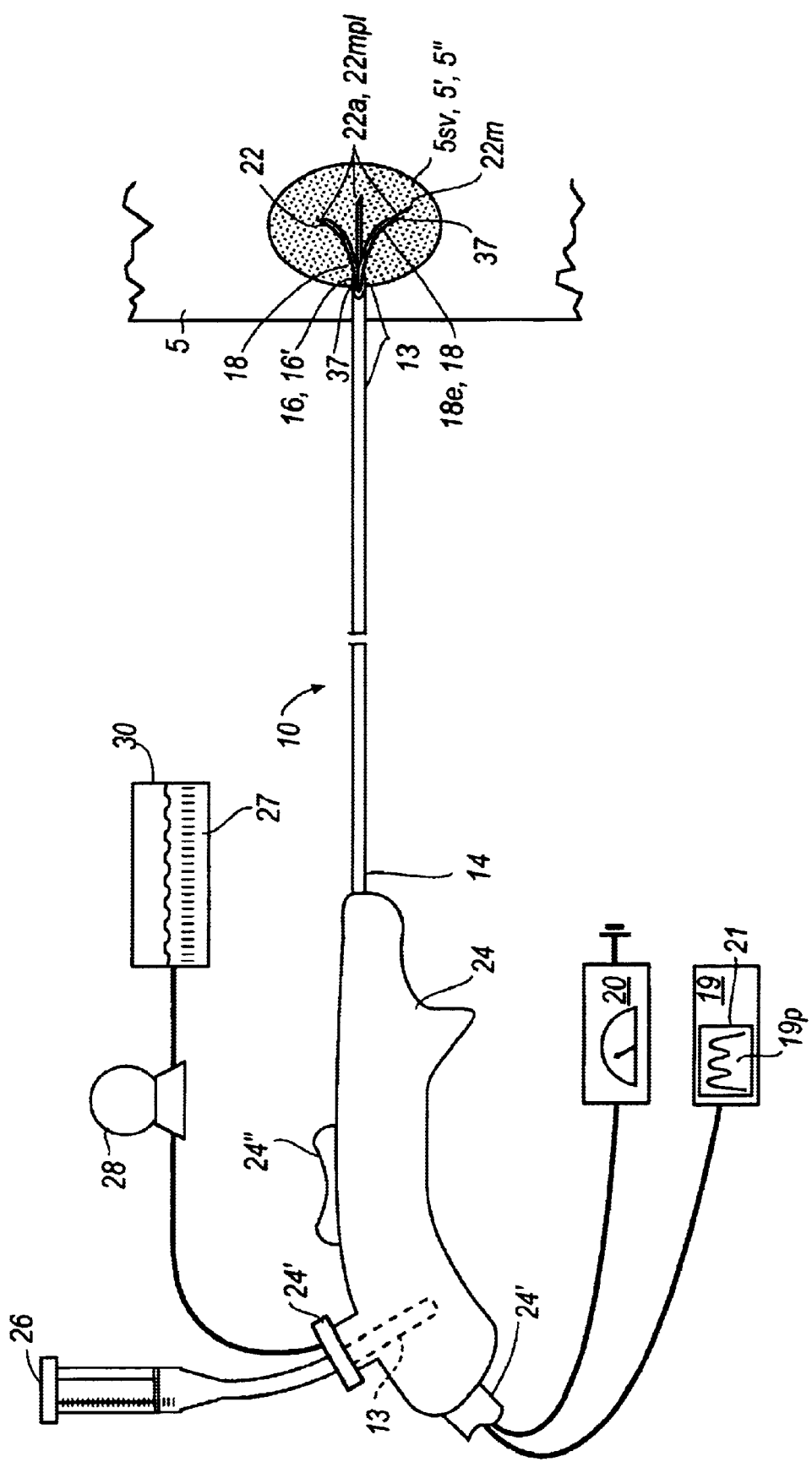
FIG. 20 is a lateral view illustrating an embodiment of a tissue biopsy and treatment apparatus with a handpiece and coupled aspiration device, fluid delivery device and fluid reservoir

Referring now to FIG. 20, in other embodiments all or portions of introducer 12 or resilient members 18 can be configured to be deflectable and/or steerable using deflection mechanisms 25 which can include pull wires 15, ratchets, cams, latch and lock mechanisms, piezoelectric materials and other deflection means known in the art. The amount of deflection of introducer 12 is selectable and can be configured to allow the maneuvering of introducer 12 through tortuous vasculator and other anatomy. In specific embodiments, the distal portions of introducer 12 can be configured to deflect 0–180° or more in up to three axes to allow the tip of introducer 12 to have retrograde positioning capability. Deflection mechanism 25 can be coupled to or integral with a moveable or slidable actuator 24", 25' on handpiece 24. Mechanism 25 and coupled actuator 25' are configured to allow the physician to selectively control the amount of deflection 25 of distal tip 16 or other portion of introducer 12. Actuator 25' can be configured to both rotate and deflect distal tip 16 by a combination of rotation and longitudinal movement of the actuator.

Referring now to FIG. 20, in various embodiments introducer 12 can be coupled at its proximal end 14 to a handle 24 or handpiece 24. Handpiece 24 can be detachable and can include ports 24' and actuators 24". Ports 24' can be coupled to one or more lumens 13 (and in turn lumens 72) and can include fluid and gas ports/connectors and electrical, optical connectors. In various embodiments, ports 24' can be configured for aspiration (including the aspiration of tissue), and the delivery of cooling, electrolytic, irrigation, polymer and other fluids (both liquid and gas) described herein. Ports 24' can include but are not limited to luer fittings, valves (one-way, two-way), toughy-bourst connectors, swage fittings and other adaptors and medical fittings known in the art. Ports 24' can also include lemo-connectors, computer connectors (serial, parallel, DIN, etc) micro connectors and other electrical varieties well known to those skilled in the art. Further, ports 24' can include opto-electronic connections which allow optical and electronic coupling of optical fibers and/or viewing scopes to illuminating sources, eye pieces, video monitors and the like. Actuators 24" can include rocker switches, pivot bars, buttons, knobs, ratchets, levers, slides and other mechanical actuators known in the art, all or portion of which can be indexed. These actuators can be configured to be mechanically, electro-mechanically, or optically coupled to pull wires, deflection mechanisms and the like allowing selective control and steering of introducer 12. Handpiece 24 can be coupled to tissue aspiration/collection devices 26, fluid delivery devices 28 (e.g. infusion pumps) fluid reservoirs (cooling, electrolytic, irrigation etc) 30 or power source 20 through the use of ports 24'. Tissue aspiration/collection devices 26 can include syringes, vacuum sources coupled to a filter or collection chamber/bag. Fluid delivery device 28 can include medical infusion pumps, Harvard pumps, syringes and the like. In specific embodiments, aspiration device 26 can be configured for performing thoracentesis which is a procedure for removing pleural fluid percutaneously.

Turning now to a discussion of resilient members 18, these members can be of different sizes, shapes and configurations with various mechanical properties selected for the particular tissue site. In one embodiment, members 18 can be needles, with sizes in the range of 28 to 12 gauge with specific embodiments of 14, 16 and 18 gauges. Resilient members 18 are configured to be in non-deployed positions while retained in introducer 12. In the non-deployed positions, resilient members 18 may be in a compacted state, spring loaded, generally confined or substantially straight if made of a suitable memory metal such as nitinol. As resilient members 18 are advanced out of introducer 12 they become distended to a deployed state, which collectively defines an ablative volume 5av, from which tissue is ablated as illustrated more fully in FIGS. 12, 19 and 16a–16c. The selectable deployment of resilient members 18 can be achieved through one or more of the following approaches (i) the amount of advancement of resilient members 18 from introducer 12; (ii) independent advancement of resilient members 18 from introducer 12; (iii) the lengths and/or sizes of energy delivery surfaces of electrodes 18 and 18'; (iv) variation in materials used for electrode 18; and (v) variation of the geometric configuration of electrode 18 in their deployed states.

As described herein, in various embodiments all or a portion of resilient member 18 can be an energy delivery device or member 18e. Turning to a discussion of energy delivery device and power sources, the specific energy delivery devices 18e and power sources 20 that can be employed in one or more embodiments of the invention include but are not limited to, the following: (i) a microwave power source coupled to a microwave antenna providing microwave energy in the frequency range from about 915 MHz to about 2.45 GHz (ii) a radio-frequency (RF) power source coupled to an RF electrode, (iii) a coherent light source coupled to an optical fiber or light pipe, (iv) an incoherent light source coupled to an optical fiber, (v) a heated fluid coupled to a catheter with a closed or at least partially open lumen configured to receive the heated fluid, (vi) a cooled fluid coupled to a catheter with a closed or at least partially open lumen configured to receive the cooled fluid (viii) a cryogenic fluid, (ix) a resistive heating source coupled to a conductive wire, (x) an ultrasound power source coupled to an ultrasound emitter, wherein the ultrasound power source produces ultrasound energy in the range of about 300 KHZ to about 3 GHz, (xi) and combinations thereof. For ease of discussion for the remainder of this application, the energy delivery device 18e is one or more RF electrodes 18e and the power source utilized is an RF power supply. For these and related embodiments, RF power 20 supply can be configured to deliver 5 to 200 watts, preferably 5 to 100, and still more preferably 5 to 50 watts of electromagnetic energy is to the electrodes of energy delivery device 18 without impeding out. The electrodes 18e are electromagnetically coupled to energy source 20. The coupling can be direct from energy source 20 to each electrode 18e respectively, or indirect by using a collet, sleeve and the like which couples one or more electrodes to energy source 20.

Figure 21A:
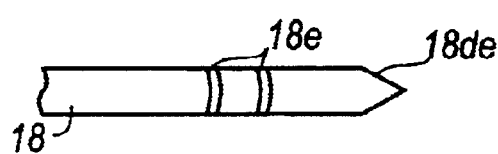
Figure 21B:
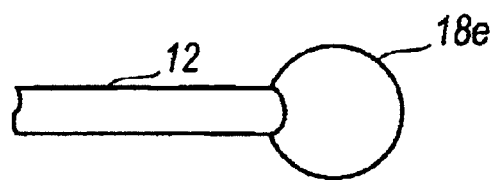
Figure 21C:
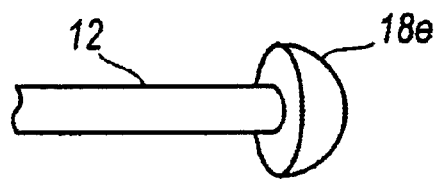
Figure 21D:
Figure 21E:
Figure 21F:
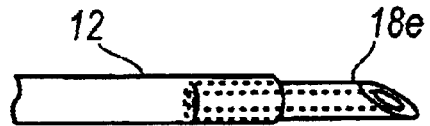
Figure 21G:
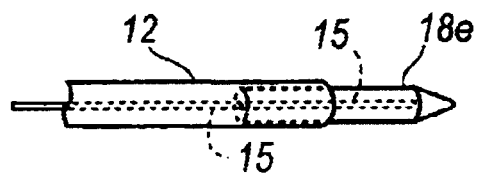
FIGS. 21g–21h are lateral views illustrating distal-end structure associated with the electrodes.
Figure 21H:
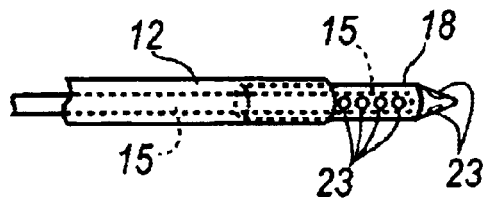

In various embodiments, electrodes 18e can have a variety of shapes and geometries. Referring now to FIGS. 21a–21f, example shapes and geometries can include, but are not limited to, ring-like (FIG. 21a), ball (FIG. 21b), hemispherical (FIG. 21c), cylindrical (FIG. 21d), conical (FIG. 21e), needle-like (FIG. 21f), and combinations thereof. FIGS. 21g and 21h show a needle electrode 18e and 18, respectively, having at least one injection port, such as ports 23, through which fluid material can be injected. Guidewire 15 is used to position the introducer 12 and/or electrode.

Figure 22:
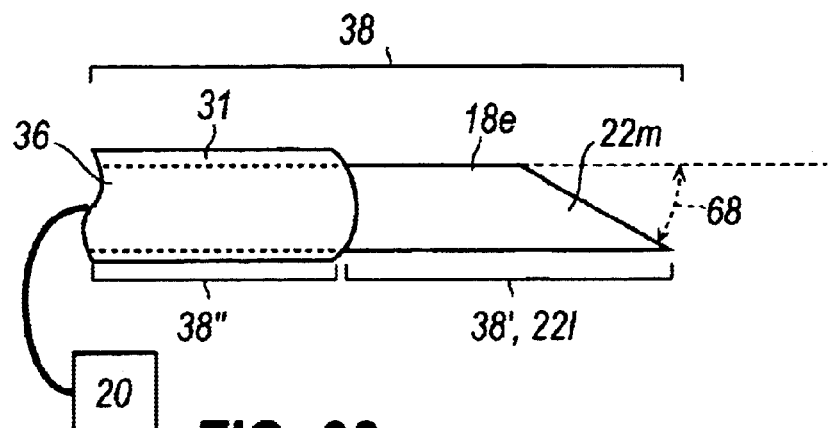
FIG. 22 is lateral view illustrating an embodiment of a needle electrode configured to penetrate tissue.

Referring to FIG. 22, in an embodiment electrode 18e can be a needle with sufficient sharpness to penetrate tissue including fibrous tissue including, encapsulated tumors cartilage and bone. The distal end 18de of electrode 18e can have a cut angle 68 that ranges from 1 to 60°, with preferred ranges of at least 25° or, at least 30° and specific embodiment of 25° and 30°. The surface of electrode 18e can be smooth or textured and concave or convex. Electrode 18e can have different lengths 38 that are advanced from distal end 16' of introducer 12. The lengths can be determined by the actual physical length of electrode(s) 18e, the length 38' of an energy delivery surface 18eds of electrode 18e and the length, 38" of electrode 18e that is covered by an insulator 36. Suitable lengths 38 include but are not limited to a range from 1–30 cms with specific embodiments of 0.5, 1, 3, 5, 10, 15 and 25.0 cm. The conductive surface area 18eds of electrode 18e can range from 0.05 mm2 to 100 cm2. The actual lengths of electrode 18e depend on the location of tissue site 5' to be ablated, its distance from the site, its accessibility as well as whether or not the physician performs an endoscopic or surgical procedure. While the conductive surface area 18eds depends on the desired ablation volume 5av to be created.

Figure 23:
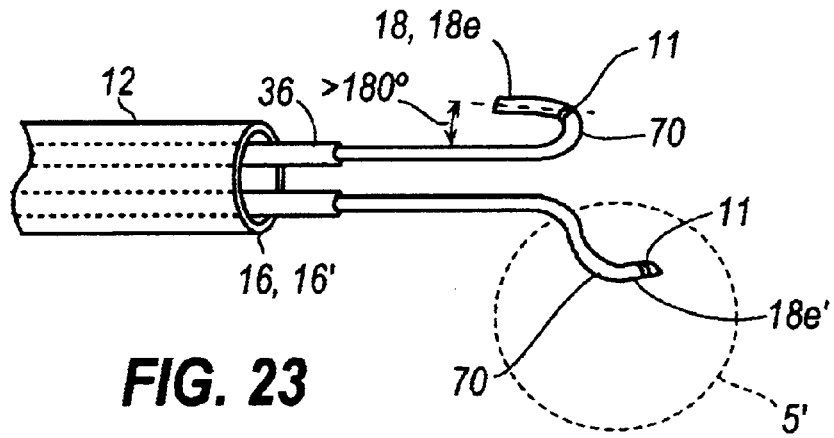
FIG. 23 is lateral view illustrating an embodiment of an electrode having at least one radii of curvature.
Figure 24:
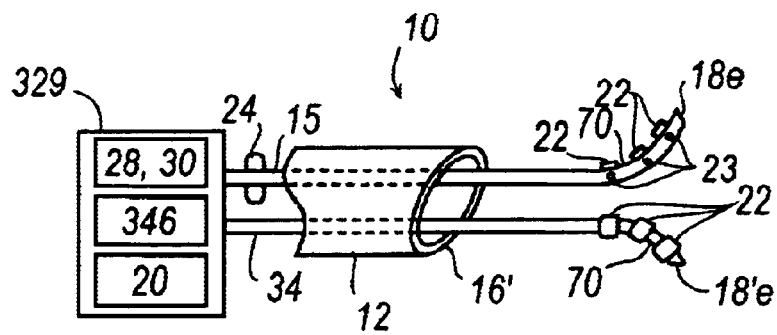
FIG. 24 is lateral view illustrating an embodiment of the electrode having a radii of curvature, sensors and a coupled advancement device.
Figure 25:
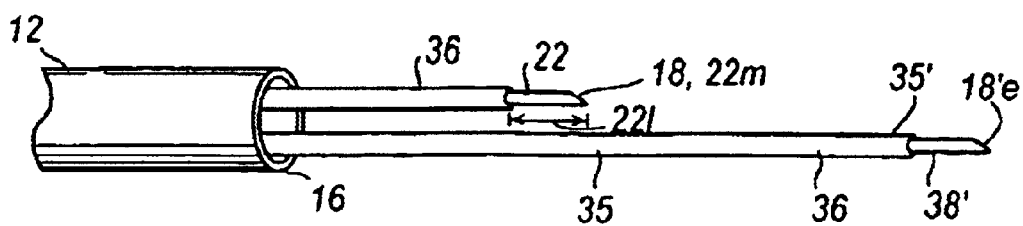
FIG. 25 is a perspective view illustrating an embodiment of the electrode that includes insulation sleeves positioned at exterior surfaces of the electrode(s) so as to define an energy delivery surface.

Referring now to FIGS. 23 and 24, electrode 18e can also be configured to be flexible and or deflectable having one or more radii of curvature 70 which can exceed 180° of curvature. In use, electrode 18e can be positioned to heat, necrose or ablate any selected target tissue volume 5'. A radiopaque marker 11 can be coated on electrodes 18e for visualization purposes. Electrode 18e can be coupled to introducer 12 and or an advancement member or device 15 or and advancement-retraction member 34 using soldering, brazing, welding, crimping, adhesive bonding and other joining methods known in the medical device arts. Also, electrode 18e can include one or more coupled sensors 22 to measure temperature and impedance (both of the electrode and surrounding tissue), voltage and current other physical properties of the electrode and adjacent tissue. Sensors 22 can be at exterior surfaces of electrodes 18e at their distal ends or intermediate sections.

Electrode 18e can be made of a variety of conductive materials, both metallic and non-metallic. Suitable materials for electrode 18e include, steel such as 304 stainless steel of hypodermic quality, platinum, gold, silver and alloys and combinations thereof. Also, electrode 18e can be made of conductive solid or hollow straight wires of various shapes such as round, flat, triangular, rectangular, hexagonal, elliptical and the like. In a specific embodiment all or portions of electrodes 18e or a second electrode 18e' can be made of a shaped memory metal, such as NiTi, commercially available from Raychem Corporation, Menlo Park, Calif.

Referring now to FIGS. 25 through 28 in various embodiments one or more electrodes 18e can be covered by an insulative layer 36 so as to have an exterior surface that is wholly or partially insulated and provides a non-insulated area which is an energy delivery surface 18eds. In an embodiment shown in FIG. 25, insulative layer 36 can comprise a sleeve that can be fixed or slidably positioned along the length of electrode 18e to vary and control the length 36' of energy delivery surface 18eds. Suitable material for insulative layer 36 include polyimide and fluorocarbon polymers such as TEFLON.

Figure 26:
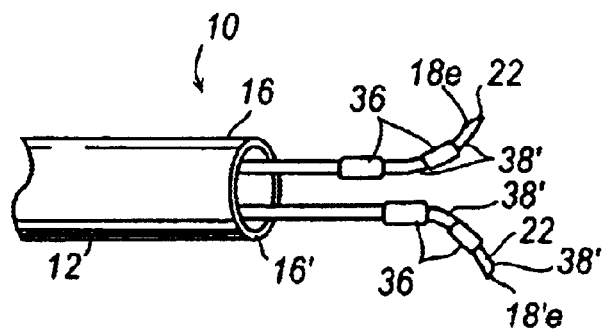
FIG. 26 is a perspective view illustrating an embodiment of the electrode that includes multiple insulation sleeves that circumferentially insulate selected sections of the electrode (s).
Figure 27:
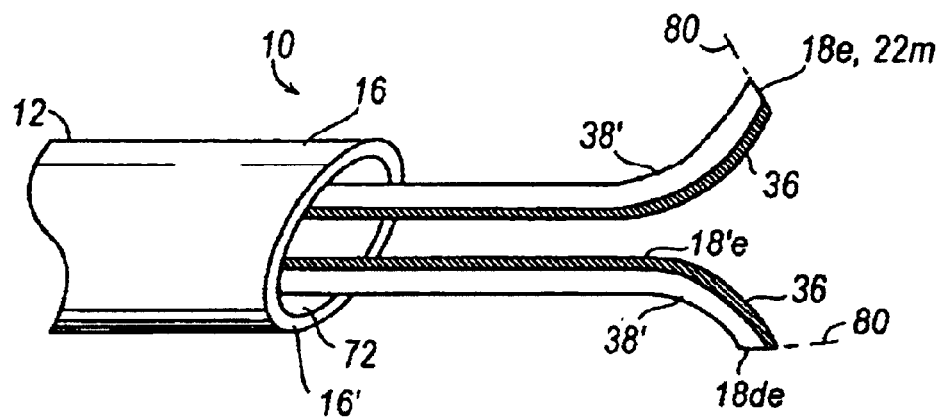
FIG. 27 is a perspective view illustrating an embodiment of the electrode with insulation that extends along longitudinal sections of the electrodes to define adjacent longitudinal energy delivery surfaces.
Figure 28:
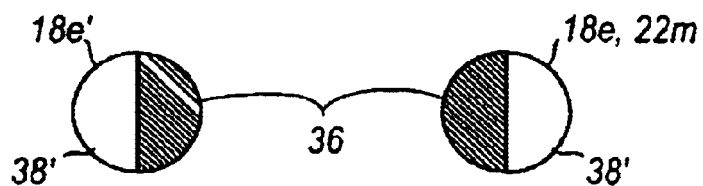
FIG. 28 is a cross-sectional view of the embodiment of FIG. 27.

In the embodiment shown in FIG. 26, insulation 36 is formed at the exterior of electrodes 18e in circumferential patterns, leaving a plurality of energy delivery surfaces 18eds. In an embodiment shown in FIGS. 27 and 28, insulation 36 extends along a longitudinal exterior surface of electrodes 18e. Insulation 36 can extend along a selected distance along a longitudinal length of electrodes 18e and around a selectable portion of a circumference of electrodes 18e. In various embodiments, sections of electrodes 18e can have insulation 36 along selected longitudinal lengths of electrodes 18e as well as completely surround one or more circumferential sections of electrodes 18e. Insulation 36 positioned at the exterior of electrodes 18e can be varied to define any desired shape, size and geometry of energy delivery surface 18eds.

Figure 29:
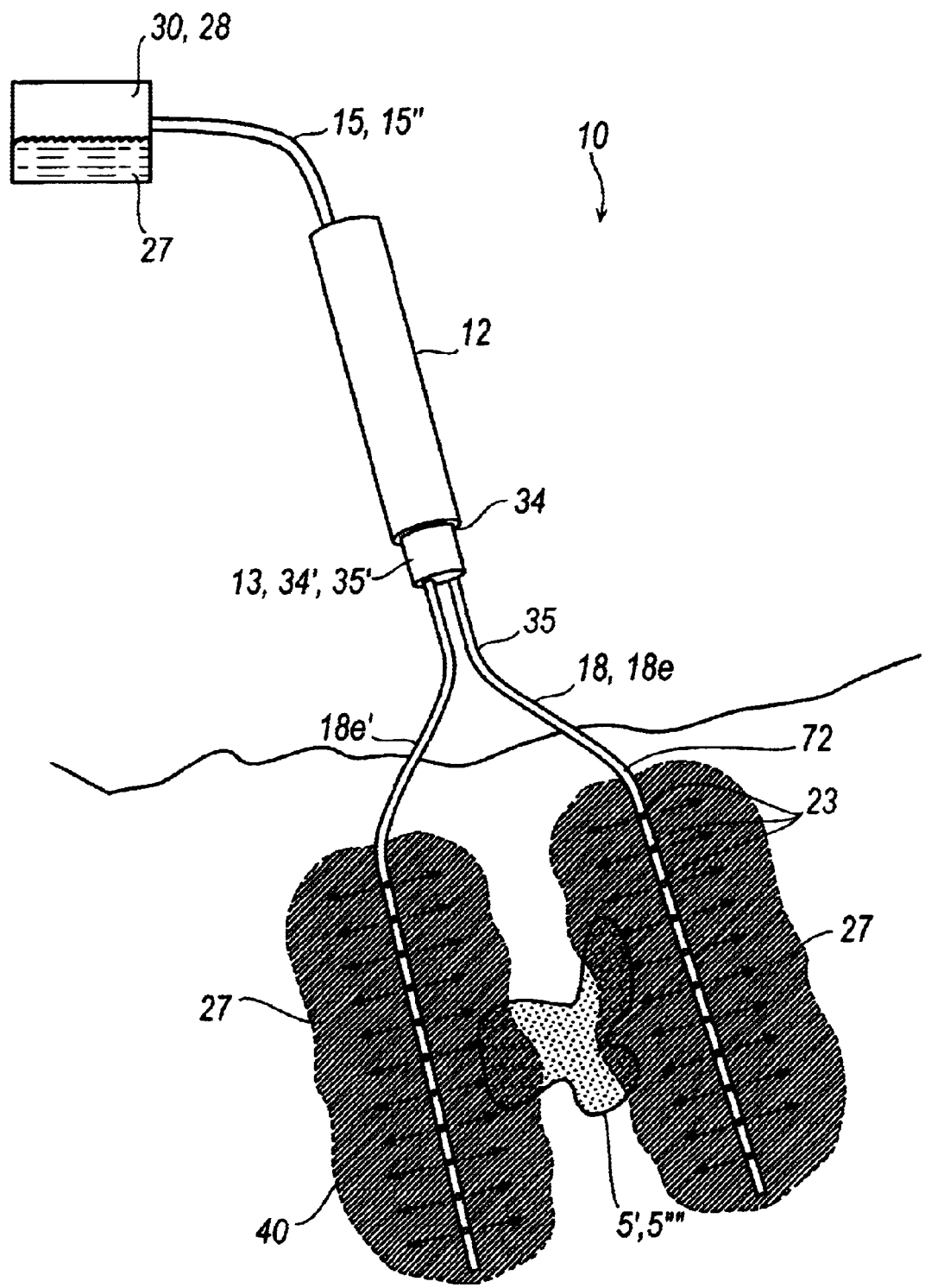
FIG. 29 is a lateral view illustrating an embodiment of the apparatus with an electrode having a lumen and apertures configured for the delivery of fluid and the use of infused fluid to create an enhanced electrode.

Referring now to FIG. 29, in various embodiments electrode 18e can include one or more lumens 72 (which can be contiguous with or the same as lumen 13) coupled to a plurality of fluid distribution ports 23 (which can be apertures 23) from which a variety of fluids 27 can be introduced, including conductivity enhancing fluids, electrolytic solutions, saline solutions, cooling fluids, cryogenic fluids, gases, chemotherapeutic agents, medicaments, gene therapy agents, photo-therapeutic agents, contrast agents, infusion media and combinations thereof This is accomplished by having ports or apertures 23 that are fluidically coupled to one or more lumens 72 coupled to lumens 13 in turn coupled to fluid reservoir 30 and/or fluid delivery device 28.

In an embodiment shown in FIG. 29, a conductivity enhancing solution 27 can be infused into target tissue site 5' including tissue mass 5". The conductivity enhancing solution can be infused before during or after the delivery of energy to the tissue site by the energy delivery device. The infusion of a conductivity enhancing solution 27 into the target tissue 5' creates an infused tissue area 5i that has an increased electrical conductivity (verses un-infused tissue) so as to act as an enhanced electrode 40. During RF energy delivery, the current densities in enhanced electrode 40 are greatly lowered allowing the delivery of greater amounts of RF power into electrode 40 and target tissue 5' without impedance failures. In use, the infusion of the target tissue site with conductivity enhancing solution provides two important benefits: (i) faster ablation times; and (ii) the creation of larger lesions; both without impedance-related shut downs of the RF power supply. This is due to the fact that the conductivity enhancing solution reduces current densities and prevents desiccation of tissue adjacent the electrode that would otherwise result in increases in tissue impedance. A preferred example of a conductivity enhancing solution is a hypertonic saline solution. Other examples include halide salt solutions, and colloidal-ferro solutions and colloidal-silver solutions. The conductivity of enhanced electrode 40 can be increased by control of the rate and amount of infusion and the use of solutions with greater concentrations of electrolytes (e.g. saline) and hence greater conductivity. In various embodiments, the use of conductivity enhancing solution 27 allows the delivery of up to 2000 watts of power into the tissue site impedance shut down, with specific embodiments of 50, 100, 150, 250, 500, 1000 and 1500 watts achieved by varying the flow, amount and concentration of infusion solution 27. The infusion of solution 27 can be continuous, pulsed or combinations thereof and can be controlled by a feedback control system described herein. In a specific embodiment, a bolus of infusion solution 27 is delivered prior to energy delivery followed by a continuous delivery initiated before or during energy delivery with energy delivery device 18e or other means.

Turning to a discussion of sensors, the use of one or more sensors 22 coupled to the introducer, energy delivery devices, deployable member and biopsy needles and permits accurate measurement of temperature at tissue site 5' in order to determine, (i) the extent of cell necrosis, (ii) the amount of cell necrosis, (iii) whether or not further cell necrosis is needed and (iv) the boundary or periphery of the ablated tissue mass. Further, sensor 22 reduces non-targeted tissue from being injured, destroyed or ablated. Referring to FIG. 24, multiple sensors can be coupled to electrodes 18.

Sensor 22 can be selected to measure temperature, tissue impedance or other tissue property described herein to permit real time monitoring of energy delivery. This reduces damage to tissue surrounding the targeted mass to be ablated. By monitoring the temperature at various points within and outside of the interior of tissue site 5', a determination of the selected tissue mass periphery can be made, as well as a determination of when cell necrosis is complete. If at any time sensor 22 determines that a desired cell necrosis temperature is exceeded, then an appropriate feedback signal is received at an energy source 20 coupled to energy delivery device 18 which then regulates the amount of electromagnetic energy delivered to electrodes 18 and 18'.

Turning now to a discussion of sensors, sensor 22 can be of conventional design, including but not limited to thermal sensors, acoutiscal sensors, optical sensors, pH sensors, gas sensors, flow sensors positional sensors and pressure/force sensors. Thermal sensors can include thermistors, thermocouples, resistive wires, optical sensors and the like. A suitable thermal sensor 22 includes a T type thermocouple with copper constantene, J type, E type, K type, fiber optics, resistive wires, thermocouple IR detectors, and the like. Acoustical sensors can include ultrasound sensors including piezoelectric sensors which can be configured in an array. Pressure and force sensors can include strain gauge sensors including silicon-based strain gauges. Optical sensors can include photomultipliers, optical diodes, fiber optics, and micro-machined optical fibers. Gas sensors can include O2 sensors such as Clark electrodes, CO2 sensors and other electrochemical based sensors known in the art. Flow/velocity sensors can include ultrasound sensors, electromagnetic sensors and aneometric sensors which can be configured to detect both liquid and gaseous flows. Positional sensors can include LVDT's, and Hall effect sensors. Other sensors which can be employed in various embodiments of the invention, include impedance sensors, antibody-based sensors, electrochemical biosensors, (e.g. glucose), gene chips, silicon-based gene chips, oligonucleotide-based gene chip sensors, and chemical sensors. In various embodiments, one sensor can be configured to detect multiple parameters or one or more sensors can be coupled together to deliver input on multiple parameters which can be multiplexed to an input device to a controller or microprocessor. Pressure sensors can be selected and/or configured to detect pressure differentials less than 1 mmHg and even less than 0.1 mmHg. In specific embodiments, pressure sensor 22 can be a micro-machined fiber optic sensor, a PSP-1 pressure sensors made Gaymar Industries Inc., (Orchard Park, N.Y.) or a Monolithic Integrated Pressure sensor made by the Fraunhofer-Institut (Duisburg, Germany). Also, ultrasound sensor or transducers can be a Model 21362 imaging probe by the Hewlett Packard Company, Palo Alto, Calif.

In various embodiments, analytical genetic methods including DNA probe methods and techniques can be utilized to monitor rates of DNA synthesis for target tissue 5' and a comparison can be made between rates of synthesis to determine cancerous versus healthy tissue. In an embodiment, sensor array 22a can be configured to detect such rates of DNA synthesis and logic resources 19/r or control system 329 can configured with algorithms to measure and determine threshold ratios of DNA synthesis as an predictor of cancerous tissue. The ratio can vary for different types of tissue (e.g. hepatic, gastro-mucosal, prostate, mucosal, submucosal etc.) and different types of cancer. Specific DNA synthesis ratios (healthy vs. target tissue) indicative of cancer can include, but are not limited to: 1:1.1, 1:1.3, 1:1.5, 1:2. 1:3, 1:5, 1:10, 1:20, 1:50 and 1:100.

An alternative embodiment of an in vivo tumor biopsy method utilizes a radiolabel marker compound bound to a tumor specific primary antibody that is detected by a radiation detection device (not shown) coupled to sensing member 22 and/or resilient member 18 and also coupled to optical detection device 19. Given the target tissue organ, prior diagnostic imaging diagnosis the physician could select among several antibodies that are likely matches to the suspected tumor. Or alternatively, he or she could start off with an antibody to many common tumors and then utilizes ones with increasing specificity as means to narrow down the tumor type. Also, a secondary label can be used as a subtraction agent to enhance sensitivity. The radiation detection device can be configured to detect alpha, gamma, beta, positron or other radioactive particle. Preferably, the label used is positron and/or has an extremely short half life (e.g. hours). The detector device can be configured to discriminate between different energies of incident radiation, e.g., between gamma radiation in different ranges within the broad 50–500 KeV range which is normally used for gamma scintillation counters and/or between alpha, gamma and beta radiation emitted by labels on the specific and a second or different antibody. Further, the detector can be configured to distinguish between the radiation emitted by the primary antibody label and that emitted by a subtraction agent, in those cases where dual antibody correction is used to enhance sensitivity. This can be achieved by embodiments having two different detector devices or by using a single detector configured to record counts of different energies in different channels, or to distinguish by other electronic means between radiation of different types or energies. In another embodiment this can be achieved by configuring coupled optical measurement device 17 with photomultiplier and comparator circuitry that detects differences in brightness of a scintillation crystal response that correlate to differences in photon energy of incident gamma radiation. The circuit can be configured to respond only to energy levels above a selected level corresponding to the desired gamma energy band for one of the two radioisotopes.

In an embodiment, the radiation detector can be a scintillation crystal optically mounted on the end of a fiber optic sensing member 22, that is configured to transmit the optical response of the crystal to incident gamma radiation to a photomultiplier and associated detection circuitry which comprise are integral or otherwise comprise optical measurement device 19. This configuration reduces the size of the detector to be compatible with a percutaneous introducing device, such as a catheter or trocar. The introducing device can be shielded to serve as a collimator, where necessary, and/or fitted with a window at a known distance from its terminus, with the scintillation crystal internally housed.

In preferred embodiments, the radionuclide label used for tumor detection is an isotope with a gamma radiation emission peak in the range of 50–500 Kev. Suitable radionuclides include but are not limited to e.g., Iodine-131, Iodine-123, Iodine-126, Iodine-133, Bromine-77, Indium-111, Indium-113 m, Copper-67, Gallium-67, Gallium-68, Ruthenium-95, Ruthenium-97, Rutenium-103, Ruthenium-105, Mercury-197, Mercury-203, Rhodium-99 m, Rhodium-101, Rhodium-105, Tellurium-121 m, Tellurium-122 m, Tellurium-125 m, Thulium-165, Thulium-167, Thulium-168, Rhenium-186, Technetium-99 m Fluorine-18. In embodiments utilizing multiple isotopes for method utilizing dual isotope correction, the two labels selected can be of sufficiently different energies to be separately detectable with the same radiation probe. Suitable such pairs of radioisotopes include, e.g., Iodine-131/Iodine 123, Gallium-67/indium-111, Iodine-131/Technetium-99 m and the like. Preferably, the paired radionuclides used for subtraction do not both have significant scatter into the channels where the emission of the other nuclide is being detected. One-way scatter can readily be corrected for by filtering algorithms known in the art.

Figure 30:
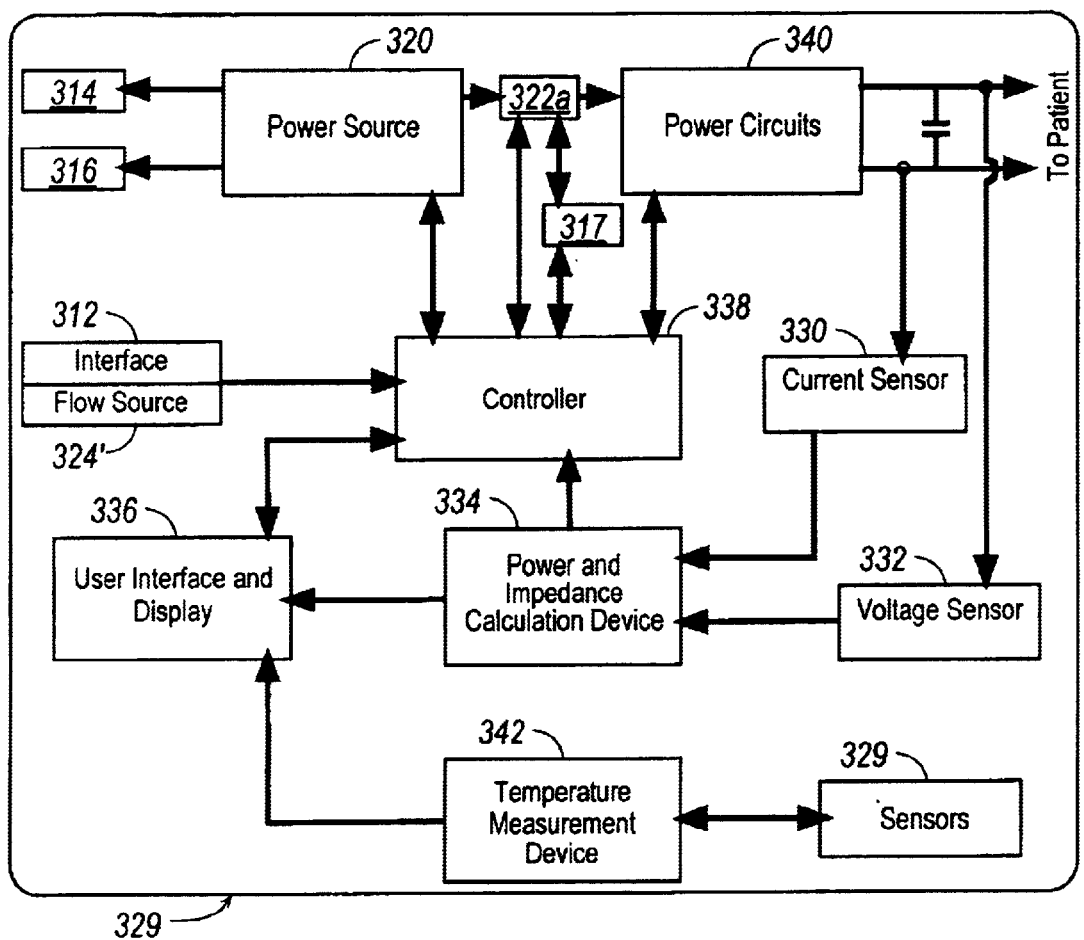
FIG. 30 is a block diagram illustrating a controller, power source, power circuits and other electronic components used with an embodiment of a control system other embodiments of the invention.
Figure 31:
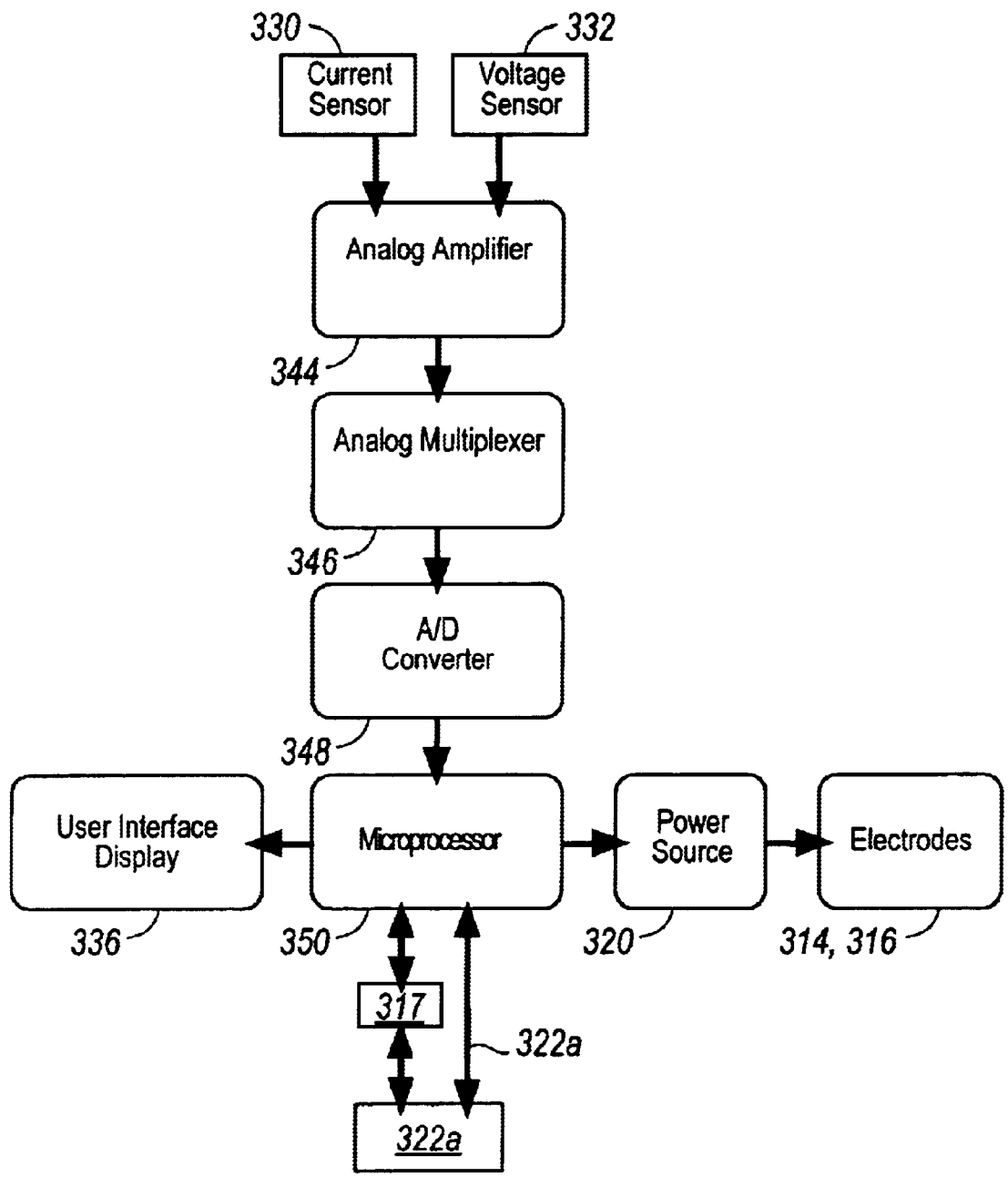
FIG. 31 is a block diagram illustrating an analog amplifier, multiplexer and microprocessor used with an embodiment of a control system or other embodiments of the invention.

Referring now to FIGS. 30 and 31, a feedback control system 329 can be connected to energy source 320, sensors 324 and energy delivery devices 314 and 316. Feedback control system 329 receives temperature or impedance data from sensors 324 and the amount of electromagnetic energy received by energy delivery devices 314 and 316 is modified from an initial setting of ablation energy output, ablation time, temperature, and current density (the "Four Parameters"). Feedback control system 329 can automatically change any of the Four Parameters. Feedback control system 329 can detect impedance or temperature and change any of the Four Parameters. Feedback control system 329 can include a multiplexer (digital or analog) to multiplex different electrodes, sensors, sensor arrays and a temperature detection circuit that provides a control signal representative of temperature or impedance detected at one or more sensors 324. A microprocessor can be connected to the temperature control circuit.

The following discussion pertains particularly to the use of an RF energy source with an optical biopsy treatment apparatus 10. For purposes of this discussion, energy delivery devices 314 and 316 will now be referred to as RF electrodes/antennas 314 and 316 and energy source 320 will now be an RF energy source. However it will be appreciated that all other energy delivery devices and sources discussed herein are equally applicable and devices similar to those associated with biopsy treatment apparatus 10 can be utilized with laser optical fibers, microwave devices and the like. The temperature of the tissue, or of RF electrodes 314 and 316 is monitored, and the output power of energy source 320 adjusted accordingly. The physician can, if desired, override the closed or open loop system.

The user of apparatus 10 can input an impedance value that corresponds to a setting position located at apparatus 10. Based on this value, along with measured impedance values, feedback control system 329 determines an optimal power and time needed in the delivery of RF energy. Temperature is also sensed for monitoring and feedback purposes. Temperature can be maintained to a certain level by having feedback control system 329 adjust the power output automatically to maintain that level.

In another embodiment, feedback control system 329 determines an optimal power and time for a baseline setting. Ablation volumes or lesions are formed at the baseline first. Larger lesions can be obtained by extending the time of ablation after a center core is formed at the baseline. The completion of lesion creation can be checked by advancing energy delivery device 316 from distal end 16' of introducer 12 to a position corresponding to a desired lesion size and monitoring the temperature at the periphery of the lesion such that a temperature sufficient to produce a lesion is attained.

The closed loop system 329 can also utilize a controller 338 to monitor the temperature, adjust the RF power, analyze the result, refeed the result, and then modulate the power. More specifically, controller 338 governs the power levels, cycles, and duration that the RF energy is distributed to electrodes 314 and 316 to achieve and maintain power levels appropriate to achieve the desired treatment objectives and clinical endpoints. Controller 338 can also in tandem analyze spectral profile 19s and perform tissue biopsy identification and ablation monitoring functions including endpoint determination. Further, controller 338 can in tandem govern the delivery of electrolytic, cooling fluid and, the removal of aspirated tissue. Controller 338 can be integral to or otherwise coupled to power source 320. In this and related embodiments, controller 338 can be coupled to light source 317 and can be configured to synchronize the delivery of pulsed power to tissue site to allow for sensing by sensors or sensor array 322a during off power off intervals to prevent or minimize signal interference, artifacts or unwanted tissue effects during sampling by sensors 324 or sensor array 322a. The controller 338 can also be coupled to an input/output (I/O) device such as a keyboard, touchpad, PDA, microphone (coupled to speech recognition software resident in controller 338 or other computer) and the like.

Referring now to FIG. 30, all or portions of feedback control system 329 are illustrated. Current delivered through RF electrodes 314 and 316 (also called primary and secondary RF electrodes/antennas 314 and 316) is measured by a current sensor 330. Voltage is measured by voltage sensor 332. Impedance and power are then calculated at power and impedance calculation device 334. These values can then be displayed at a user interface and display 336. Signals representative of power and impedance values are received by controller 338 which can be a microprocessor 338.

A control signal is generated by controller 338 that is proportional to the difference between an actual measured value, and a desired value. The control signal is used by power circuits 340 to adjust the power output in an appropriate amount in order to maintain the desired power delivered at the respective primary and/or secondary antennas 314 and 316. In a similar manner, temperatures detected at sensors 324 provide feedback for maintaining a selected power. The actual temperatures are measured at temperature measurement device 342, and the temperatures are displayed at user interface and display 336. A control signal is generated by controller 338 that is proportional to the difference between an actual measured temperature, and a desired temperature. The control signal is used by power circuits 340 to adjust the power output in an appropriate amount in order to maintain the desired temperature delivered at the respective sensor 324. A multiplexer 346 can be included to measure current, voltage and temperature, at the numerous sensors 324 as well as deliver and distribute energy between primary electrodes 314 and secondary electrodes 316.

Controller 338 can be a digital or analog controller, or a computer with embedded, resident or otherwise coupled software. In an embodiment controller 338 can be a Pentium® family microprocessor manufacture by the Intel® Corporation (Santa Clara, Calif.). When controller 338 is a computer it can include a CPU coupled through a system bus. On this system can be a keyboard, a disk drive, or other non-volatile memory systems, a display, and other peripherals, as are known in the art. Also coupled to the bus are a program memory and a data memory. In various embodiments controller 338 can be coupled to imaging systems, including but not limited to ultrasound, CT scanners (including fast CT scanners such as those manufacture by the Imatron Corporation (South San Francisco, Calif.), X-ray, MRI, mammographic X-ray and the like. Further, direct visualization and tactile imaging can be utilized.

User interface and display 336 can include operator controls and a display. In an embodiment user interface 336 can be a PDA device known in the art such as a Palm® family computer manufactured by Palm® Computing (Santa Clara, Calif.). Interface 336 can be configured to allow the user to input control and processing variables, to enable the controller to generate appropriate command signals. Interface 336 can also receives real time processing feedback information from one or more sensors 324 for processing by controller 338, to govern the delivery and distribution of energy, fluid etc.

The output of current sensor 330 and voltage sensor 332 is used by controller 338 to maintain a selected power level at primary and secondary antennas 314 and 316. The amount of RF energy delivered controls the amount of power. A profile of power delivered can be incorporated in controller 338, and a preset amount of energy to be delivered can also be profiled.

Circuitry, software and feedback to controller 338 results in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 324. A controller 338 can be incorporated into feedback control system 329 to switch power on and off, as well as modulate the power. Also, with the use of sensor 324 and feedback control system 329, tissue adjacent to RF electrodes 314 and 316 can be maintained at a desired temperature for a selected period of time without causing a shut down of the power circuit to electrode 314 due to the development of excessive electrical impedance at electrode 314 or adjacent tissue.

Referring now to FIG. 31, current sensor 330 and voltage sensor 332 are connected to the input of an analog amplifier 344. Analog amplifier 344 can be a conventional differential amplifier circuit for use with sensors 324. The output of analog amplifier 344 is sequentially connected by an analog multiplexer 346 to the input of A/D converter 348. The output of analog amplifier 344 is a voltage which represents the respective sensed temperatures. Digitized amplifier output voltages are supplied by A/D converter 348 to a microprocessor 350. Microprocessor 350 may be a Power PC® chip available from Motorola or an Intel® Pentium® Series chip. However, it will be appreciated that any suitable microprocessor or general purpose digital or analog computer can be used to calculate impedance or temperature or perform image processing and tissue identification functions.

Microprocessor 350 sequentially receives and stores digital representations of impedance and temperature. Each digital value received by microprocessor 350 corresponds to different temperatures and impedances. Calculated power and impedance values can be indicated on user interface and display 336. Alternatively, or in addition to the numerical indication of power or impedance, calculated impedance and power values can be compared by microprocessor 350 with power and impedance limits. When the values exceed predetermined power or impedance values, a warning can be given on user interface and display 336, and additionally, the delivery of RF energy can be reduced, modified or interrupted. A control signal from microprocessor 350 can modify the power level supplied by energy source 320 to RF electrodes 314 and 316. In a similar manner, temperatures detected at sensors 324 provide feedback for determining the extent and rate of (i) tissue hyperthermia (ii) cell necrosis; and (iii) when a boundary of desired cell necrosis has reached the physical location of sensors 324.

Conclusion

It will be appreciated that the applicants have provided a novel and useful apparatus and method for the biopsy and treatment of tumors using minimally invasive methods. The foregoing description of a preferred embodiment of the invention has been presented for purposes of illustration and description. It is not intended to be exhaustive or to limit the invention to the precise forms disclosed. Embodiments of the invention can be configured for the biopsy and treatment of tumor and tissue masses in a number of organs including but no limited to the liver, breast, bone and lung. However, embodiments of the invention are applicable to other organs and tissue as well. Obviously, many modifications and variations will be apparent to practitioners skilled in this art. Further, elements from one embodiment can be readily recombined with elements from one or more other embodiments. Such combinations can form a number of embodiments within the scope of the invention. It is intended that the scope of the invention be defined by the following claims and their equivalents.

What is claimed is:

1. A tissue biopsy and treatment apparatus for detecting and treating tumors, the apparatus comprising:
   an elongated delivery device including a lumen, the elongated delivery device being maneuverable in tissue;
   a sensor array deployable from the elongated delivery device, the sensor array including a plurality of resilient members each having a tissue piercing distal portion, at least one of the plurality of resilient members being positionable in the elongated delivery device in a compacted state and deployable with curvature into tissue from the elongated delivery device in a deployed state, at least one of the plurality of resilient members including an optical sensor operatively connected to function as an emitter and a detector, the sensor array having a geometric configuration adapted to volumetrically sample tissue at a tissue site or identify tissue at a tissue site, and an optical switching device to switch a mode of said optical sensor;
   at least some of said resilient members being electrodes which can be coupled to an RF energy source for ablating tissue when electrical energy is supplied to the electrodes from the source; and
   wherein the sensor array is configured to measure a spectral profile of at least one portion of the tissue site.

2. The apparatus of claim 1, wherein the at least one portion includes a first portion and a second portion, the sensor array being configured to substantially simultaneously measure a first spectral profile of the first portion and a second spectral profile of the second portion.

3. The apparatus of claim 1, further comprising:
   logic resources coupled to one of the sensor array, or the sensor; and
   wherein the logic resources are configured to identify or differentiate tissue responsive to a signal from one of the sensor or the sensor array.

4. The apparatus of claim 3, wherein the logic resources are configured to distinguish between normal and abnormal tissue, wherein the abnormal tissue includes at least one of abnormally mutated tissue, abnormally dividing tissue, cancerous tissue, metastatic tissue, immortal tissue, or hypoxic tissue.

5. The apparatus of claim 3, wherein the logic resources are configured to locates position of the energy delivery device relative to one of a tumor mass or an ablation volume.

6. The apparatus of claim 5, wherein the logic resources are operatively connected to one of a monitoring device or a display device to signal the position of the energy delivery device relative to the tumor mass or to the ablation volume.

7. The apparatus of claim 6, wherein the logic resources are configured to interface with the display device to graphically display the position of the energy delivery device relative to the tumor mass or the ablation volume.

8. The apparatus of claim 3, wherein the logic resources are configured to identify a clinical endpoint for a tissue ablation procedure.

9. The apparatus of claim 1, wherein the optical sensor comprises at least one of a light conducting member or an optical fiber positionable within a lumen of at least one of the plurality of resilient members, wherein the light conducting member or the optical fiber is coupled to a light source or a coherent light source.

10. The apparatus of claim 9, wherein the sensor comprises an emitting and a detecting optical fiber positionable within the lumen of the at least one resilient member.

11. The apparatus of claim 1, wherein the plurality of resilient members includes a first resilient member having a first lumen with a first positionable optical sensing member and a second resilient member having a second lumen with a second positionable optical sensing member.

12. The apparatus of claim 11, wherein the, first sensing member is a first optical fiber configured as an emitter and a detector and the second optical sensing member is a second optical fiber configured as an emitter and a detector.

13. The apparatus of claim 1, at least one of the plurality of resilient members including a second sensor is configured to detect a change in a tissue property.

14. The apparatus of claim 13, wherein the property includes at least one of a physiologic property, a metabolic property, a thermal property, a temperature, an electrical property, an impedance, an optical property, an absorbance, a reflectance, a dimensional property, and a pH.

15. The apparatus of claim 1, wherein the sensor array is configured to detect an indicator of cell necrosis.

16. The apparatus of claim 15, wherein the indicator of cell necrosis is selected from the group consisting of a tissue vapor bubble, a rate of tissue vapor bubble formation, a denatured tissue protein, a denatured DNA, and an intracellular fluid.

17. The apparatus of claim 1, wherein the sensor array is configured to distinguish between non cancerous and cancerous tissue.

18. The apparatus of claim 1, further comprising:
at least one of (i) the elongated delivery device or (ii) at least one of the plurality of the plurality of resilient members being adapted for fluid delivery therethrough to an infusion port disposed on at least one of the elongated delivery device or at least one resilient member of the plurality of resilient members.

19. The apparatus of claim 1, further comprising:
a handpiece coupled to one of the elongated delivery device or the sensor array; and
a first advancement device at least partially positionable in one of the handpiece or the elongated delivery device, the advancement device being configured to advance at least one of the plurality of resilient members.

20. The apparatus of claim 19, further comprising:
a second advancement device at least partially positionable in one of the handpiece or the elongated delivery device, the second advancement device configured to advance a second resilient member of the at least one plurality of resilient members independent of an advancement of the first advancement device.

21. A tissue biopsy and treatment apparatus for detecting and treating tumors, the apparatus comprising:
an elongated delivery device including a lumen, the elongated delivery device being maneuverable in tissue;
a sensor array deployable from the elongated delivery device, the sensor array including a plurality of resilient members each having a tissue piercing distal portion, at least one of the plurality of resilient members being positionable in the elongated delivery device in a compacted state and deployable with curvature into tissue from the elongated delivery device in a deployed state, at least one of the plurality of resilient members including an optical sensor operatively connected to function as an emitter and a detector, the sensor array having a geometric configuration adapted to volumetrically sample and measure a spectral profile of at least one portion of a tissue site to differentiate or identify tissue at the tissue site, and an optical switching device to switch a mode of said optical sensor; and
at least some of said resilient members being electrodes which can be coupled to an RF energy source for ablating tissue when electrical energy is supplied to the electrodes from the sources.

22. A tissue biopsy and treatment apparatus for detecting and treating tumors, the apparatus comprising:
an elongated delivery device including a lumen, the elongated delivery device being maneuverable in tissue;
a sensor array deployable from the elongated delivery device, the sensor array including a plurality of resilient members each having a tissue piercing distal portion, at least one of the plurality of resilient members being positionable in the elongated delivery device in a compacted state and deployable with curvature into tissue from the elongated delivery device in a deployed state, at least one of the plurality of resilient members including an optical sensor operatively connected to function as an emitter and a detector, the sensor array having a geometric configuration adapted to volumetrically sample tissue at a tissue site or identify tissue at a tissue site, and an optical switching device to switch a mode of said optical sensor;
at least some of said resilient members being electrodes which can be coupled to an RF energy source for ablating tissue when electrical energy is supplied to the electrodes from the source;
wherein the sensor includes a first sensor and a second sensor; and
wherein at least one of the first or the second sensors is selected from the group consisting of an emitter, an electromagnetic emitter, an optical emitter, an acoustical emitter, a lasers and an LED.

23. The apparatus of claim 22, wherein the emitter is substantially positioned within a volume defined by the sensor array.

24. The apparatus of claim 22, wherein the emitter is substantially positioned outside of a volume defined by the sensor array.

25. The apparatus of claim 22, wherein the emitter emits a reference signal and a probe signal.

26. The apparatus of claim 25, wherein the sensor includes a third sensor adapted to detect the reference signal.

27. The apparatus of claim 26, wherein the third sensor is adapted to detect the reference signal with substantially no effect from tissue.

28. The apparatus of claim 27, wherein the third sensor is positioned substantially adjacent or in proximity to the emitter.

29. The apparatus of claim 22 wherein the emitter is configured to emit electromagnetic energy over a selectable frequency range.

30. A tissue biopsy and treatment apparatus for detecting and treating tumors, the apparatus comprising:
  an elongated delivery device including a lumen, the elongated delivery device being maneuverable in tissue;
  a sensor array deployable from the elongated delivery device, the sensor array including a plurality of resilient members each having a tissue piercing distal portion, at least one of the plurality of resilient members being positionable in the elongated delivery device in a compacted state and deployable with curvature into tissue from the elongated delivery device in a deployed state, at least one of the plurality of resilient members including an optical sensor operatively connected to function as an emitter and a detector, the sensor array having a geometric configuration adapted to volumetrically sample tissue at a tissue site or identify tissue at a tissue site, and an optical switching device to switch a mode of said optical sensor;
  at least some of said resilient members being electrodes which can be coupled to an RF energy source for ablating tissue when electrical energy is supplied to the electrodes from the source; and
  wherein the sensor array is configured to detect a marking agent.

31. The apparatus of claim 30, wherein the sensor array is configured to detect an absence of the marking agent.

32. The apparatus of claim 30, wherein the sensor array is configured to obtain one of an improved resolution or an improved sensitivity.

33. The apparatus of claim 30, comprising:
  a source of marking agent fluidically coupled to one of the elongated delivery device or at least one of the plurality of resilient members.

34. The apparatus of claim 33, wherein the marking agent is selected from the group consisting of an optical marker, a fluorescent marker, a radioactive-marker, a temperature sensitive marker, an antibody, a liposome, an antibody-coated liposome, a microsphere, and a chemotherapeutic agent.

35. The apparatus of claim 33, wherein the marking agent is reactive to a delivery of energy.

36. The apparatus of claim 33, wherein the marking agent is configured to enhance at least one of the delivery of energy to a least a portion of the tumor volume or the degree of thermal injury to the at least a portion of the tumor volume.

37. The apparatus of claim 36, wherein the at least a portion of the tumor volume is a selectable portion.

38. The apparatus of claim 33, wherein the marking agent includes a plurality of marking agents.

39. The apparatus of claim 38, wherein the plurality of marking agents include a first marking agent configured to mark a first tissue condition or first tissue type and a second marking agent configured to mark a second tissue condition or a second tissue type.

40. The apparatus of claim 39, wherein at least one of the first or the second tissue conditions is a cancerous tissue condition.

41. The apparatus of claim 39, wherein at least one of the first or second tissue conditions is selected from the group consisting of a thermal injury condition, a tissue necrosis, a tissue ablation, a tissue vaporization, a tissue coagulation, and a cell membrane rupture.

42. The apparatus of claim 39, wherein the first tissue condition is a cancerous condition and the second tissue condition is a thermal injury condition.

43. The apparatus of claim 39, wherein the first tissue condition is a first tissue temperature and the second condition is a second tissue temperature.

44. The apparatus of claim 43, wherein the second tissue temperature is selected from the group consisting of a tissue injuring temperature, a tissue necrosing temperature, a tissue ablative temperature, and a tissue vaporization temperature.

45. The apparatus of claim 39, wherein the plurality of marking agents includes a third marking agent.

46. The apparatus of claim 38, wherein the plurality of marking agents includes a first marking agent coupled to a first marking agent carrier, wherein the first marking agent carrier is configured to release the first marking agent at a selectable temperature, tissue condition or tissue chemical concentration.

47. The apparatus of claim 46, wherein the selectable temperature is in the range of about 40° C. to about 60° C.

48. The apparatus of claim 46, wherein the selectable temperature is in the range of about 45° C. to about 55° C.

49. The apparatus of claim 46, wherein the plurality of marking agents includes a second marking agent coupled to a second marking agent carrier, wherein the second marking agent carrier is configured to release the first marking agent at a selectable temperature.

50. The apparatus of claim 49, wherein the second selectable temperature is in the range of about 40° C. to about 60° C.

51. The apparatus of wherein the second selectable temperature is in the range of about 45° C. to about 55° C.

52. The apparatus of claim 33, wherein the marking agent is configured to detect one of a gene, a gene fragment, a genetic variant, a genetic mutation, a DNA sequence, a DNA fragment and an expressed sequence tag.

* * * * *

UNITED STATES PATENT AND TRADEMARK OFFICE
CERTIFICATE OF CORRECTION

PATENT NO. : 6,869,430 B2
DATED : March 22, 2005
INVENTOR(S) : Daniel J. Balbierz and Theodore Johnson It is certified that error appears in the above-identified patent and that said Letters Patent is hereby corrected as shown below:

Title page,
Item [30], Foreign Application Priority Data, please remove
"Mar. 23, 2000      (JP) ........................2000-087109".

Signed and Sealed this

Twenty-ninth Day of November, 2005

JON W. DUDAS
*Director of the United States Patent and Trademark Office*